United States Patent [19]

Lipkovker

[11] Patent Number: 5,421,816

[45] Date of Patent: Jun. 6, 1995

[54] ULTRASONIC TRANSDERMAL DRUG DELIVERY SYSTEM

[75] Inventor: Lev M. Lipkovker, Bellevue, Wash.

[73] Assignee: Endodermic Medical Technologies Company, Mt. Vernon, Wash.

[21] Appl. No.: 961,113

[22] Filed: Oct. 14, 1992

[51] Int. Cl.⁶ ............................................. A61B 17/00
[52] U.S. Cl. ....................................................... 604/20
[58] Field of Search ............... 128/633, 635, 736, 767, 128/24 AA, 804; 604/20, 22, 289, 290, 890.1, 892.1; 601/2; 607/154

[56] References Cited

U.S. PATENT DOCUMENTS

| | | | |
|---|---|---|---|
| 4,029,084 | 6/1977 | Soldner . | |
| 4,309,989 | 1/1982 | Fahim . | |
| 4,372,296 | 2/1983 | Fahim | 128/24 AA |
| 4,657,543 | 4/1987 | Langer et al. | 604/646 |
| 4,767,402 | 8/1988 | Kost et al. | 604/290 |
| 4,787,888 | 11/1988 | Fox | 604/20 |
| 4,821,740 | 4/1989 | Tachibana et al. | 604/290 |
| 4,948,587 | 8/1990 | Kost et al. | 424/435 |
| 4,953,565 | 9/1990 | Tachibana et al. | 604/290 |
| 5,007,438 | 4/1991 | Tachnibana et al. . | |
| 5,016,615 | 5/1991 | Driller et al. . | |
| 5,019,034 | 5/1991 | Weaver et al. | 604/20 |
| 5,053,001 | 10/1991 | Reller et al. | 604/20 |
| 5,080,646 | 1/1992 | Theeuwes et al. | 604/20 |
| 5,084,008 | 1/1992 | Phipps | 604/20 |
| 5,115,805 | 5/1992 | Bommannan et al. | 128/24 AA |
| 5,135,478 | 8/1992 | Sibalis | 604/20 |
| 5,171,215 | 12/1992 | Flanagan | 604/22 |
| 5,231,975 | 8/1993 | Bommannan et al. | 604/20 |
| 5,267,985 | 12/1993 | Shimada | 604/290 |

FOREIGN PATENT DOCUMENTS 2756460  6/1979  Germany .
WO91/12772  9/1991  WIPO .

OTHER PUBLICATIONS

Donald M. Skauen and Gaylen M. Zentner, "Phonophoresis," *International Journal of Pharmaceutics*, 20 (1984), pp. 235–245.

(List continued on next page.)

*Primary Examiner*—Lee S. Cohen
*Assistant Examiner*—Samuel Gilbert
*Attorney, Agent, or Firm*—Christensen, O'Connor, Johnson & Kindness

[57] ABSTRACT

Ultrasonic energy is used to release a stored drug and forcibly move the drug through the skin of an organism into the blood stream. A housing (81) includes a cavity (67) defined by an assembly of ultrasonic transducers (65) and separated from the skin by a polymeric membrane (69) that stores the drug to be delivered. The ultrasonic transducer assembly includes a flat, circular ultrasonic transducer (85) that defines the top of a truncated cone and a plurality of transducer segments (87a, 87b, 87c, 87d . . . ) that define the walls of the cone. The resonant frequency of the planar transducer is lower than the resonant frequency of the transducer segments. The planar, flat, circular transducer generates fixed frequency (5 KHz–1 MHz range) ultrasonic stimuli impulses for a predetermined period of time (10–20 seconds). Between the stimuli pulse periods, the transducer segments receive variable frequency ultrasonic pumping pulses. Preferably, the variable frequency ultrasonic pumping pulses lie in the 50 MHz–300 MHz range. The variable frequency ultrasonic pumping pulses are applied to opposed transducer segments. The transducer segments create beams that impinge on the skin at an oblique angle and create a pulsating wave. Further, the variable frequency ultrasonic pumping pulses are applied to opposing transducer segments in a rotating manner to create pulsating waves in the skin in a variety of directions. The stimuli pulses cause the planar transducer to produce an ultrasonic wave that excites the local nerves in the way that trauma (heat, force) excites the local nerves. The nerve excitation opens the epidermal/dermal junction membrane and the capillary endothelial cell joints. The variable frequency ultrasonic pumping pulses cause the transducer segments to produce ultrasonic waves in both the polymeric membrane and the skin. The ultrasonic waves pump the drug first through the polymeric membrane and then through, skin openings into the underlying blood vessels.

120 Claims, 21 Drawing Sheets

OTHER PUBLICATIONS

Katsuro Tachibana, "Transdermal Delivery of Insulin to Alloxan-Diabetic Rabbits by Ultrasound Exposure," *Pharmaceutical Research*, vol. 19, No. 7, 1992, pp. 109-111.

D. Bommannan, Hirohisa Okuyama, Paul Stauffer, and Richard H. Guy, "Sonophoresis. I. The Use of High--Frequency Ultrasound to Enhance Transdermal Drug Delivery," *Pharmaceutical Research*, vol. 9, No. 4, 1992, pp. 559-564.

D. Bommannan, Gopinathan K. Menon, Hirohisa Okuyama, Peter M. Elias, and Richard H. Guy, "Sonophoresis. II. Examination of the Mechanism(s) of Ultrasound-Enhanced Transdermal Drug Delivery," *Pharmaceutical Research*, vol. 9, No. 8, 1992, pp. 1043-1047, J. C. McElnay, T. A. Kennedy, and R. Harland, "The influence of ultrasound on the percutaneous absorption of fluocinolone acetonide," *International Journal of Pharmaceutics*, 40 (1987), pp. 105-110.

Motoaki Shichiri, Yoshimitsu Yamasaki, Ryuzo Kawamori, Nobuyoshi Hakui, and Hiroshi Abe, "Wearable Artificial Endocrine Pancreas with Needle-type Glucose Sensor," *The Lancet*, Nov. 20, 1982, pp. 1129-1131.

Deborah Erickson, "Skinside Out," *Scietific American*, Nov. 1991, pp. 129-130.

Joseph Kost, "Ultrasound induced delivery of peptides," *Journal of Controlled Release*, 24 (1993), pp. 247-255.

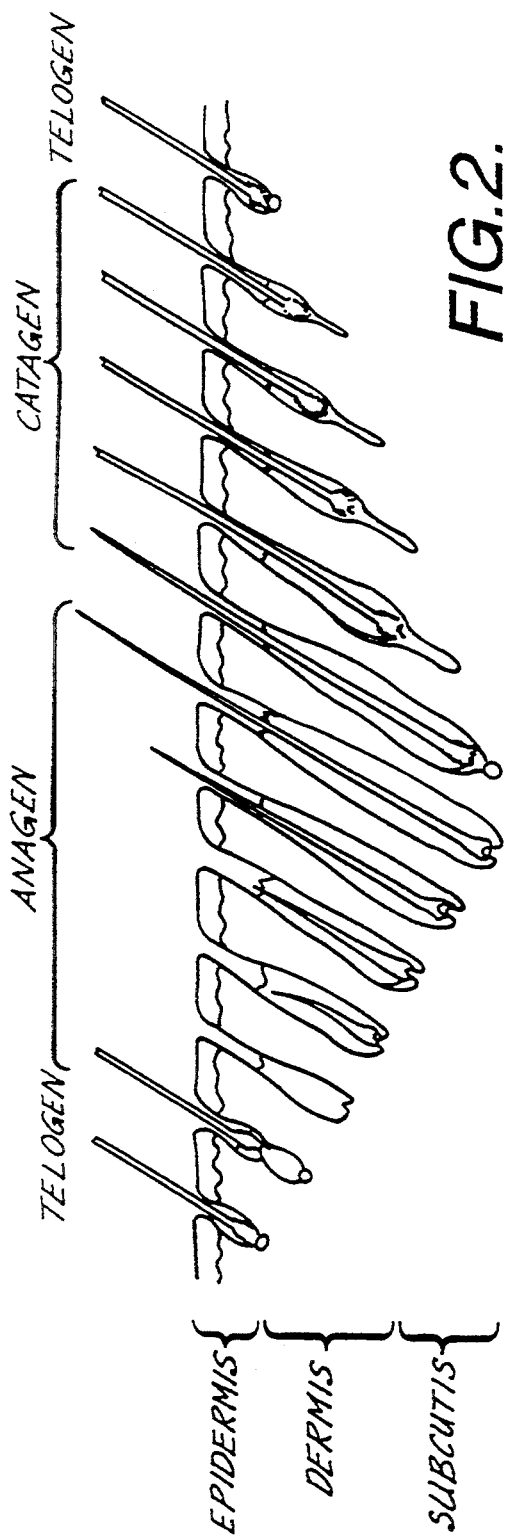
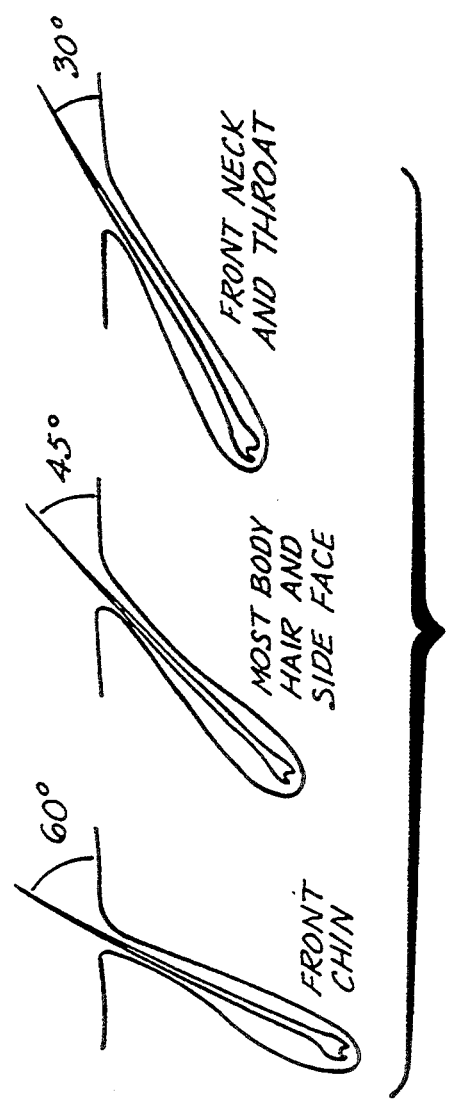
FIG.2.
FIG.3.

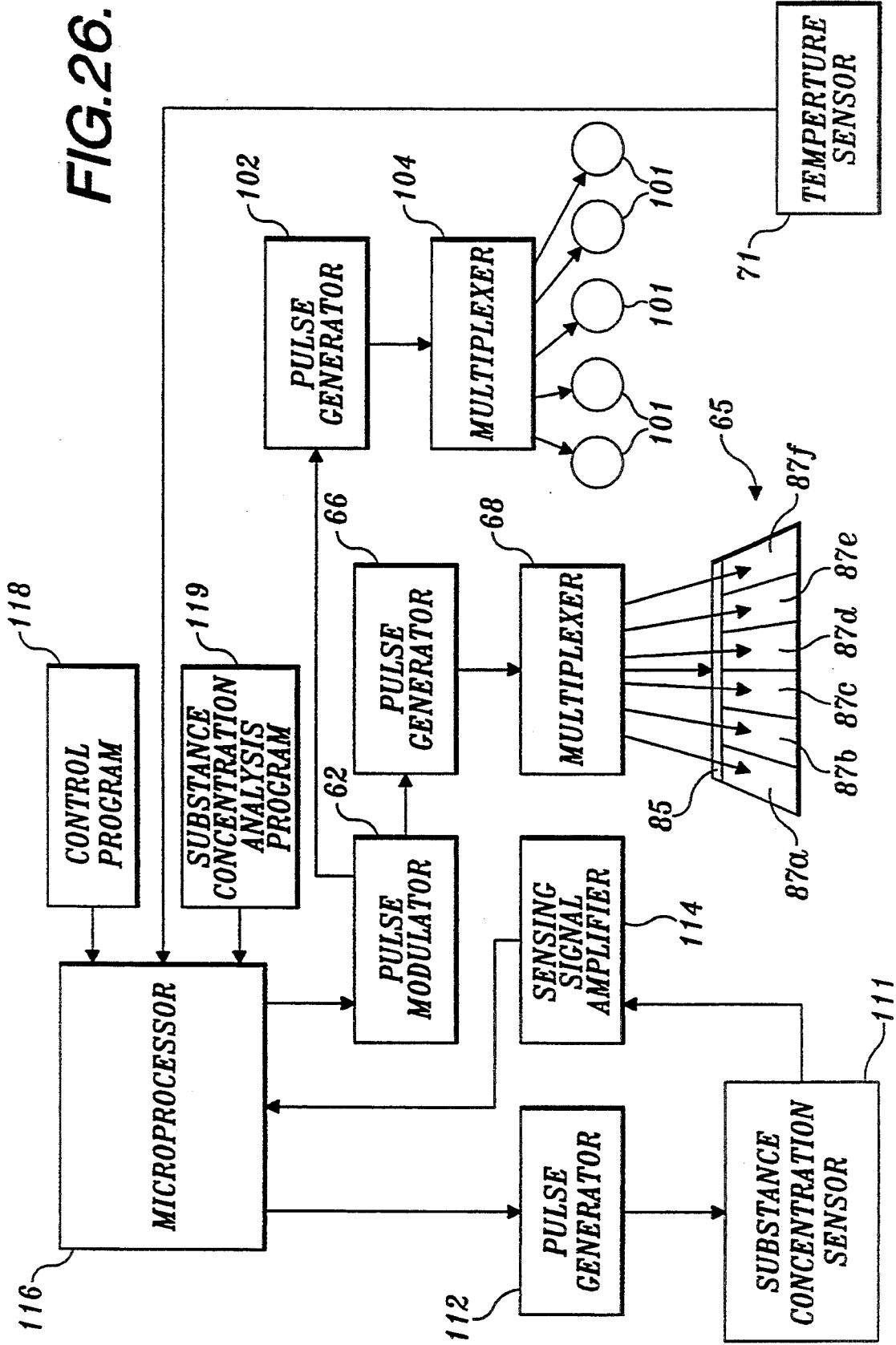

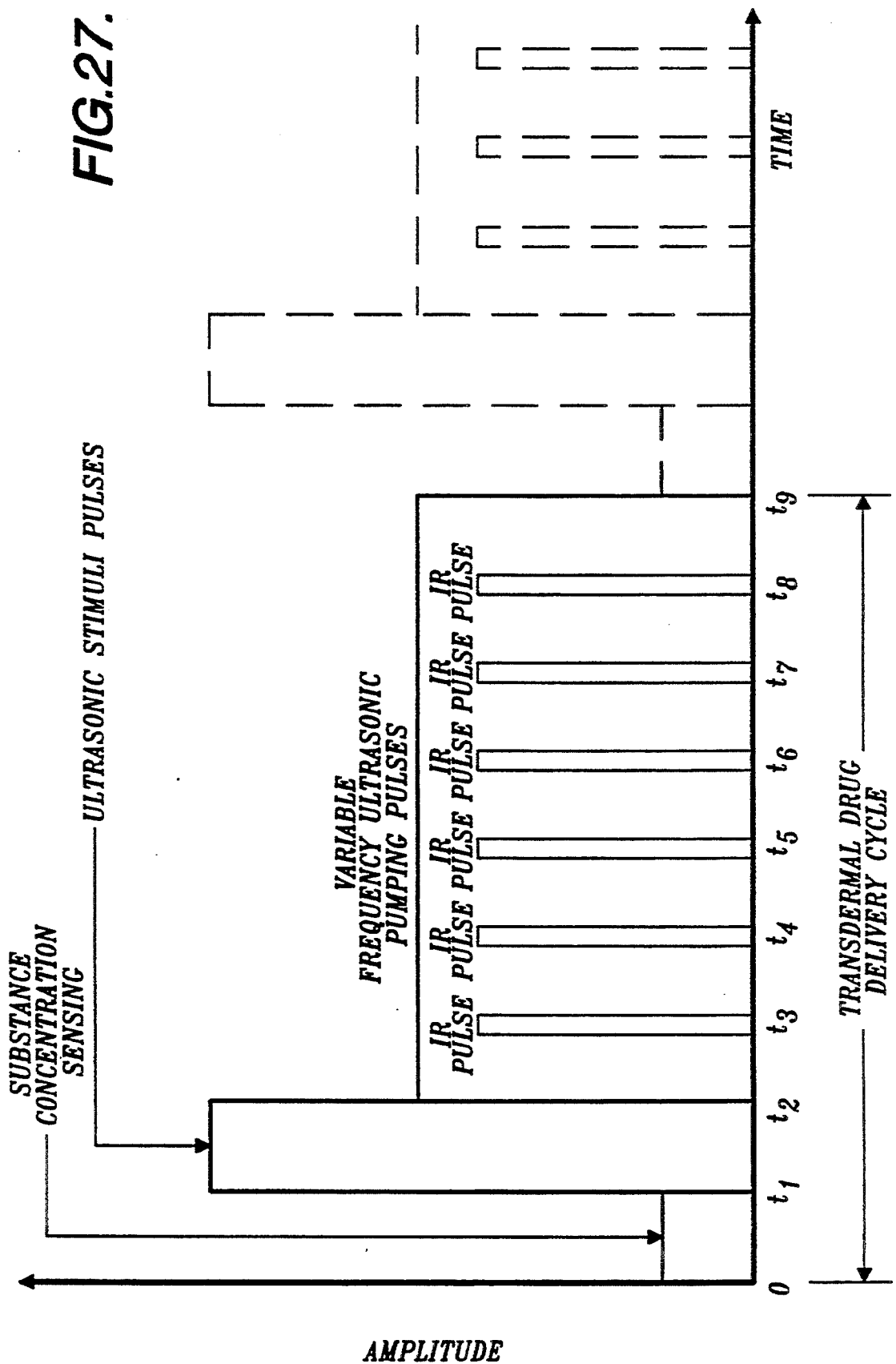

ULTRASONIC TRANSDERMAL DRUG DELIVERY SYSTEM

TECHNICAL AREA

This invention relates to drug delivery systems and, more particularly, to transdermal drug delivery systems.

BACKGROUND OF THE INVENTION

A vast majority of pharmaceutical agents (e.g., drugs) in clinical use today are given either orally or by injection. While injection provides a fast and direct route to the blood stream, injection often causes pain and anxiety and, occasionally, contamination. Further, injection does not provide for a constant or sustained delivery of drugs. Finally, when a drug is injected by a syringe, the entire dose is placed in the body and cannot be withdrawn should an adverse reaction occur.

Oral administration subjects the pharmaceutical agent to hepatic metabolism. Hepatic metabolism substantially degrades the effectiveness of pharmaceutical agents, up to 90 percent in some cases. More specifically, the first organ that receives an intestine absorbed drug taken orally is the liver. The liver detoxifies molecules that are foreign to the body. Most drug molecules are considered by the liver to be foreign. As a result, a significant quantity of a particular medicine may never reach the rest of the body due to the liver's detoxifying the drug's molecules. The degree of detoxification varies from person to person and may account for adverse reactions in some people and not others by influencing the amount of a drug that is left for absorption by the remainder of the body. More importantly, the decrease in effectiveness due to hepatic metabolism by the liver leads to increases in the amount of the agent being administered, which leads to undesirable side effects and gastric intolerance. That is, the amount taken by mouth is usually more than the body needs, often resulting in adverse side effects. Further, because dosage requirements often vary from individual to individual, it is difficult to tailor individual dosages using the predefined amounts determined by manufacturers of orally administered drugs. Finally, as with a syringe injection, when a drug is taken by mouth and absorbed, the entire dose is in the body. If an adverse reaction takes place it is difficult to remove the drug to stop the reaction. Nevertheless, oral administration presently is the most preferred way of giving pharmaceutical agents due to the ease of administration and avoidance of the need for invasive vascular access, as required by injections.

The adult skin structure can be broken into three layers. The stratum corneum, which is actually part of the epidermal layer, is the first layer of skin defense against the exterior environment. The stratum corneum is capable of absorbing superficial trauma while still maintaining adequate protection against loss of water and ingress of micro organisms and other substances. The stratum corneum layer is 15-20 cells thick. In many areas of the human body, the stratum corneum layer is very thin, often below several microns. The intercellular space of the stratum corneum is approximately 30 percent by volume. The intercellular space is filled by lipid composition, which is ideally suited to form a transport barrier. The inner layer of the stratum corneum is in contact with granular cells (very moist) and the outer layer is in contact with a dry environment. Thus a substantial water content gradient exists across the stratum corneum.

The second layer is the epidermal layer, which consists of epidermal cells bound together by tight junctions into a viscoelastic matrix. Between the junctions lie heavily convoluted lipid-filled extracellular spaces containing a host of cellular lymphocytic factors, enzymes and other anti-microbial agents. The epidermal layer is the body's prime protective barrier. Its basal cells provide metabolic and additional water barrier functions. The epidermal barrier provides a formidable defense structure even in the absence of the stratum corneum, especially to water-soluble agents that do not possess a lipid extracellular phase. Enzyme activity may be controlled or rendered inactive by employing chemical, enzymic or heat treatment.

The innermost layer is the dermal layer. The dermal layer consists of basal germ cells positioned upon a basal membrane with known permeability of approximately 40 kilodaltons and below. Unless specific excitation factors are present, large molecular weight materials cannot cross the basal membrane.

Below the basal membrane are the majority of the capillary loops that comprise the terminal states of the microcirculation tree (i.e., the blood vessels) of the human organisms. The capillary loops are the target of current passive transdermal drug delivery systems (described below). Because a very large number of capillary loops are present, large surface areas are available for the systemic exchange of fluids.

Penetrating all three skin layers are numerous hair follicles in various growth states—telogen, anagen and catagen. The hair follicle growth stage correlates with the depth of the follicle, late-anagen follicles being the deepest and closest to the most heavily developed capillary blood supply. The centerline of the hair follicle is positioned less than five microns from the encircling capillary blood supply. The stratum corneum follows the invagination of the follicles at the skin level, terminating approximately half-way down the follicles. The sensory nerve network that surrounds the follicles responds to any physical excitation on the hair shaft. Thus, a highly sensitive responsive system is present in the hair follicle regions of the skin. Follicle density on skin surfaces varies depending upon location from $100/cm^2$ to $900/cm^2$.

Other than by syringe, there are two methods by which drugs can be delivered through the skin—passive and active diffusion. Passive diffusion involves placing a concentration of drug in a reservoir on the surface of the skin and allowing the drug to passively diffuse through the skin into the body. Since there are natural barriers in the skin which keep almost all molecules from entering the body through the skin, only a few molecules from the reservoir of the drug pass through the skin and are absorbed first by the blood stream and then by the body.

Due to natural skin barriers, few pharmaceuticals have been successfully diffused through the skin and into the subdermal microcirculation regions of the human body, i.e., the underlying blood vessels. The most successful drugs to be diffused through the skin are clonidine, nitroglycerin, scopolamine, and estradiol. Because these drugs are effective at very low plasma concentrations, they can be applied using small passive skin patches. A 10 ng/ml plasma concentration has been arbitrarily adopted by the industry as a mean figure above which passive transdermal drug delivery is not effective. This concentration level eliminates the possibility of passive transdermal delivery of such highly successful agents as aspirin, which requires a concentration of 150,000 ng/ml to be effective. Currently, acetaminophen, cimetidine, and indomethacin cannot be delivered by passive transdermal drug delivery systems.

In addition to concentration level, molecular size is an issue with the passive diffusion of drug absorption. The skin's natural barriers limit or prevent absorption of medicaments that are composed of large molecules. Therefore, with passive diffusion, if a medicine is to be effective in the body, it must work well at very low dosages and be of a molecular size that the skin will allow to enter the body. While chemical enhancers have been investigated as solutions to allow for greater dosage absorption through the skin by passive diffusion, none have worked well enough to pass the Federal Drug Administration (FDA) requirements and/or be successful commercially.

A potentially more viable way for drugs to transcend the skin's barriers is to use an active energy source that "pushes" or "pulls" drug molecules through the skin and, at the same time controls, the rate of delivery. An energy driven system will allow a greater quantity of the medicine to be delivered in a shorter or variable time frame. Potentially an energy driven system will permit larger molecular weight drugs to transcend the barriers of the skin in a short time period.

Two types of active transdermal drug delivery have been proposed. The first, which is called iontophoresis, is a system that uses a direct current of electricity to charge drugs. Electrically charged drugs are driven into the skin. To date, there is only one medicine, Lidocaine, used in such a device. Lidocaine is a drug used for local anesthesia. Extensive investigation is presently being conducted by the pharmaceutical industry on the use of iontophoresis for drug delivery. While this method of delivery is slow, it probably will increase the number of medicaments used for transdermal drug delivery. Furthermore, delivery is better controlled, when compared to passive diffusion.

The other method of active drug delivery uses ultrasound as the energy source. For a variety of reasons, the results of drug delivery by this method have traditionally been inconsistent. Results of previous experiments have been difficult to repeat. More specifically, it has been known for several decades that ultrasound radiation pressure applied to drug molecules in contact with skin can increase transdermal penetration rate. The mechanism of action has been unclear with some researchers citing boundary stirring effect, some citing microchannel production via cavitation and others citing direct radiation pressure onto the drug, pumping it into the skin.

Some researchers have conducted studies of the interaction of ultrasound and specific drug formulations. Some researchers have applied an ultrasonic field to drug molecules themselves, rather than to the skin and associated structures. Other researchers have shown that ultrasound is effective in shearing polymeric compositions of drugs contained in transdermal patches. The intent of these researchers was to modulate the release rate of a drug from a polymeric matrix. Finally, some researchers have applied ultrasound to the skin itself. The following U.S. patents describe some of the results of the foregoing research: U.S. Pat. Nos. 4,657,543; 4,767,402; 4,780,212; 4,821,740; 4,948,587; 4,953,565; and 5,007,438. Also see Patent Cooperation Treaty (PCT) application No. 91/12772 and German Patent No. 27 56 460. Most, if not all, of the foregoing patents show a lack or no control of application direction, little or no control of frequency and power levels, no control of duty cycle and ignorance of a host of other controlling factors.

Various criteria for drug delivery enhancer design have been established. They are: (i) the enhancer should elicit no pharmacological response; (ii) the enhancer should be specific in its action; (iii) the enhancer should act immediately with a predictable duration and its action should be reversible; (iv) the enhancer should be chemically and physically stable, and be compatible with all of the components of the drug formulation; (v) the enhancer should be odorless, colorless, and tasteless; and (vi) the enhancer should be nontoxic, nonallergenic, and a nonirritant. These criteria can be conveniently applied with slight modification to all transdermal drug delivery enhancement approaches, both chemical and nonchemical. No single drug delivery enhancement approach available today meets all of the foregoing criteria. Organic enhancers produce a characteristic foul taste in the mouth shortly after skin application. Several alcohol or solvent-based enhancers cause severe skin irritation and can lead to an eczematous reaction. Device-based enhancers such as iontophoretic titrators come closer to satisfying all of the criteria, but fall short in broad spectrum general applicability, specificity of action, reversibility of action and nonirritability.

As will be better understood from the following discussion, the present invention is directed to providing an active transdermal drug delivery system that enhances the diffusion of large molecular weight substances (e.g., large molecular weight drugs) between an external device-based reservoir and the subdermal microcirculation tree of an organism, such as the human body. This result is achieved by using ultrasonic energy to excite the skin system of the organism in a way that allows multifrequency, multidirectional subsurface waves to diffuse large molecular weight substances through the skin in an efficient and controllable manner.

SUMMARY OF THE INVENTION

In accordance with this invention, an ultrasonic transdermal drug delivery system is provided. More specifically, a transdermal drug delivery system formed in accordance with this invention includes ultrasonic transducers that create ultrasonic waves. The ultrasonic waves release a stored pharmaceutical agent (e.g., a drug) and forcibly move the agent through the skin of an organism, such as the human body, into the blood vessels underlying the transducers. The transdermal drug delivery system includes a housing having a reservoir for storing the drug to be released. The reservoir is separated from the skin by an ultrasonically controllable polymeric membrane. Alternatively, the ultrasonically controllable polymeric membrane can store the drug to be released. An adhesive attaches the delivery system to the skin. The cavity is defined by an assembly of ultrasonic transducers. The ultrasonic transducer assembly includes a stimuli transducer for creating an ultrasonic stimuli wave in the skin of an organism and at least one pumping (drug delivery) transducer for moving the drug through the polymeric membrane and the skin into the blood vessels of the organism. Control electronics, preferably stored in the housing, control the operation of the stimuli transducer and the at least one pumping transducer.

In accordance with other aspects of this invention, the transducer assembly has the shape of a truncated cone.

In accordance with further aspects of this invention, the stimuli transducer is located in the top of the cone and the at least one pumping transducer is located in the wall of the cone.

In accordance with additional aspects of this invention, the top of the cone is defined by the stimuli transducer, which has a fiat, circular shape, and the walls of the cone are defined by a plurality of transducer segments each of which forms a pumping transducer. Preferably, the resonant frequency of the fiat, circular transducer is less than the resonant frequency of the transducer segments.

In accordance with yet other aspects of this invention, located between the transducers and the reservoir is a drug-impermeable laminate that also functions as a focusing lens for the transducers.

In accordance with still other aspects of this invention, the control electronics apply ultrasonic stimuli pulses to the skin by energizing the stimuli transducer at a first frequency, preferably lying in the 5 KHz–1 MHz range for a predetermined period of time (10–20 seconds). Between the stimuli pulse periods, the control electronics apply variable frequency ultrasonic pumping pulses to the skin by energizing the pumping transducer segments. Preferably, the frequency of the variable frequency ultrasonic pumping pulses lie in the 50 MHz–300 MHz range.

In accordance with yet further aspects of this invention, a skin temperature sensor is positioned in the housing to sense the temperature of the skin receiving the drug. The temperature information is used by the control electronics to prevent the ultrasonic waves from overheating the skin.

In accordance with still further aspects of this invention, the drug delivery system also includes one or more additional stimuli transducers, such as infrared (IR) or laser emitters, in the housing. The additional stimuli transducers emit stimuli pulses at selected intervals during the variable frequency ultrasonic pumping portion of the operational cycle. The additional stimuli pulses enhance the operation of the drug delivery system by heating the skin and/or creating additional ultrasonic waves in the skin.

In accordance with yet still further aspects of this invention, the variable frequency, ultrasonic pumping pulses are applied to opposed transducer segments.

In accordance with yet still other aspects of this invention, the variable frequency, ultrasonic pumping pulses are applied to alternate pairs of transducer segments in a rotational manner.

In accordance with yet still additional aspects of this invention, the drug delivery system includes a sensor for sensing drug delivery effectiveness and using the resultant information to control the rate of drug delivery.

In accordance with still yet other aspects of this invention, the sensor, which may function as a stand-alone device, includes a cavity, an ultrasonic transducer, a focusing lens, and a substance sensing transducer located in the cavity, plus energizing electronics for the ultrasonic transducer and a test data processor for evaluating the output of the substance sensing transducer. The cavity is juxtaposed against the skin and the ultrasonic transducer and focusing lens are sized evenly and energized to cause body fluid to be drawn into the cavity.

In summary, the invention provides a new and improved transdermal drug delivery system. The transdermal drug delivery system is an active system that uses ultrasonic waves to enhance drug delivery. Relatively low frequency ultrasonic pulses excite or stimulate the nervous system of an organism, such as the human body, similarly to the way the nervous system is excited by skin trauma, such as heat or a blow to the skin. As is well understood by those skilled in the medical arts, skin trauma stimulation causes both the dermal-epidermal junction (i.e., the basal) membrane and the capillary endothelial joints to open so that fluids can be moved to the area of the trauma. The invention takes advantage of these openings to pump drugs from a reservoir through the skin into the capillary loops which form the ends of the microcirculation tree of the organism. Pumping is accomplished by applying variable frequency ultrasonic pumping pulses to the skin by energizing the pumping transducer segments between stimulation pulses. Because the transducer segments that receive the variable frequency ultrasonic pumping pulses form the walls of a truncated cone, the ultrasonic waves produced by the transducers impinge on the underlying skin at an oblique angle. The ultrasonic waves create a pumping action that first creates large openings on the surface of the skin for the initial receipt of drugs in a first layer of skin cells. The received drugs are pumped through the skin as the wave alternately moves the skin cells away from and then toward one another in an inward direction. The drug is also forced through the aperture surrounding the hair follicles and through the sweat glands of the organism.

In essence, ultrasound is used by this invention to open channels in the skin surface and then literally pushes a medicament which has been dissolved in a fluid through the channels between the cells in the second layer of skin, the epidermis. The ultrasound also opens the cells in the deepest layer of the skin, the dermis. The dermis is a layer of cells one cell thick which controls the immunology of the skin and produces cells which migrate to the top surface of the skin to renew the stratum corneum. Ordinarily, this layer is closed to permeation except for certain stimulations, such as trauma, local infection or chemical irritation, for example through an insect bite. The ultrasound opens the basal layer of the dermis. In addition to the skin, the ultrasound pumps medicants through the channels surrounding hair follicles and sweat gland pores. Large quantities of many drugs (including those with large molecules) can be administered through the skin using the present invention.

Clusters or loops of blood vessel capillaries located directly beneath the skin basal layer and surround the hair follicles and sweat gland pores receive the administered medicant. Once the medicant enters the capillaries, it is absorbed into the systemic or blood circulation of the body and delivered to where it is needed.

In some embodiments of the invention, additional stimulation is provided by IR or laser emitters during the pumping portion of the cycle. Excess heating of the skin is prevented by terminating stimulation of skin when heating exceeds a predetermined level. Further, feedback control of drug delivery is provided in some embodiments of the invention. A novel sensor determines the magnitude of a substance contained in the plasma and interstitial fluid of the body that relates to the effort of the drug being delivered. The sensor includes an ultrasonic transducer and a focusing lens constructed and oriented in a way that withdraws fluid into a cavity that houses a substance sensing transducer. The sensor can be used as a stand-alone device separate and apart from a drug delivery system.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 is a sequence of diagrams illustrating the growth cycle of a hair follicle;

FIG. 3 is a series of diagrams illustrating the typical angle of insertion of hair follicles in different regions of the human body;

FIG. 26 is a block diagram of the electronic control portion of the ultrasonic transdermal drug delivery system illustrated in FIG. 25;

FIG. 27 is a timing diagram illustrating the drug delivery cycle of the embodiment of the invention illustrated in FIG. 25;

DETAILED DESCRIPTION OF THE PREFERRED EMBODIMENTS

As will be better understood from the following description, the present invention provides an active transdermal drug delivery system that uses ultrasonic energy to both excite the skin in a manner that "fools" the nervous system of an organism and pump a pharmaceutical agent (e.g., a drug) from a reservoir through the skin to the capillary loops just below the skin surface. Prior to describing the presently preferred embodiments of the invention, in order for the invention to be more easily understood, a brief description of the skin is set forth.

Figure 1:
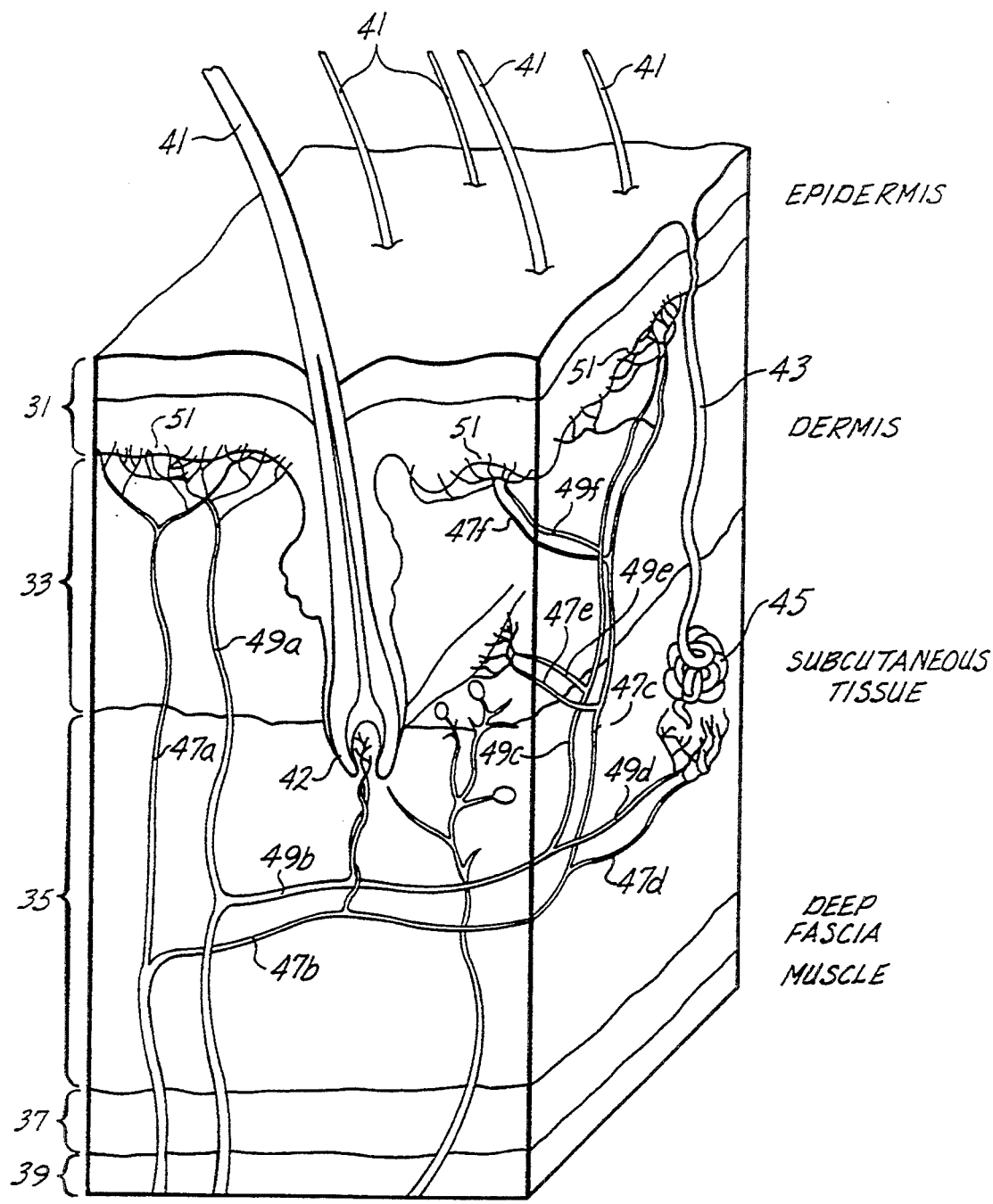
FIG. 1 is a three-dimensional view of a section of the skin of the human body.

As shown in FIG. 1, the skin includes two primary layers—the epidermis 31 and the dermis 33. Located beneath the dermis 33 is subcutaneous tissue 35 followed by deep fascia 37 and, then, muscle 39. Extending through the epidermis 31 and the dermis 33 are hair follicles 41. As shown in FIG. 2, depending on their age, hair follicles terminate in a dermis layer 33 or in the epidermis or subcutaneous tissue near the dermis layer. As shown in FIG. 3, the angle of hair follicles varies between 30° and 60° depending upon the location of a follicle.

Sweat pores 43 (FIG. 1) extend through the dermis and epidermis layers 31 and 33, terminating at sweat glands 45 located in the subcutaneous tissue 35. Extending through the muscle 39, the fascia 37 and the subcutaneous tissue 35 are branches 47a, 47b, 47c . . . and 49a, 49b, and 49c . . . of the venous and arterial systems of the organism. The veins and artery branches terminate at capillary loops 51, which comprise the terminal stages of the microcirculation tree of the organism. Capillary loops are located at the dermal-epidermal interface, the bulbous regions of the hair follicles, adjacent the sweat glands 45, and in a variety of other areas.

Figure 4:
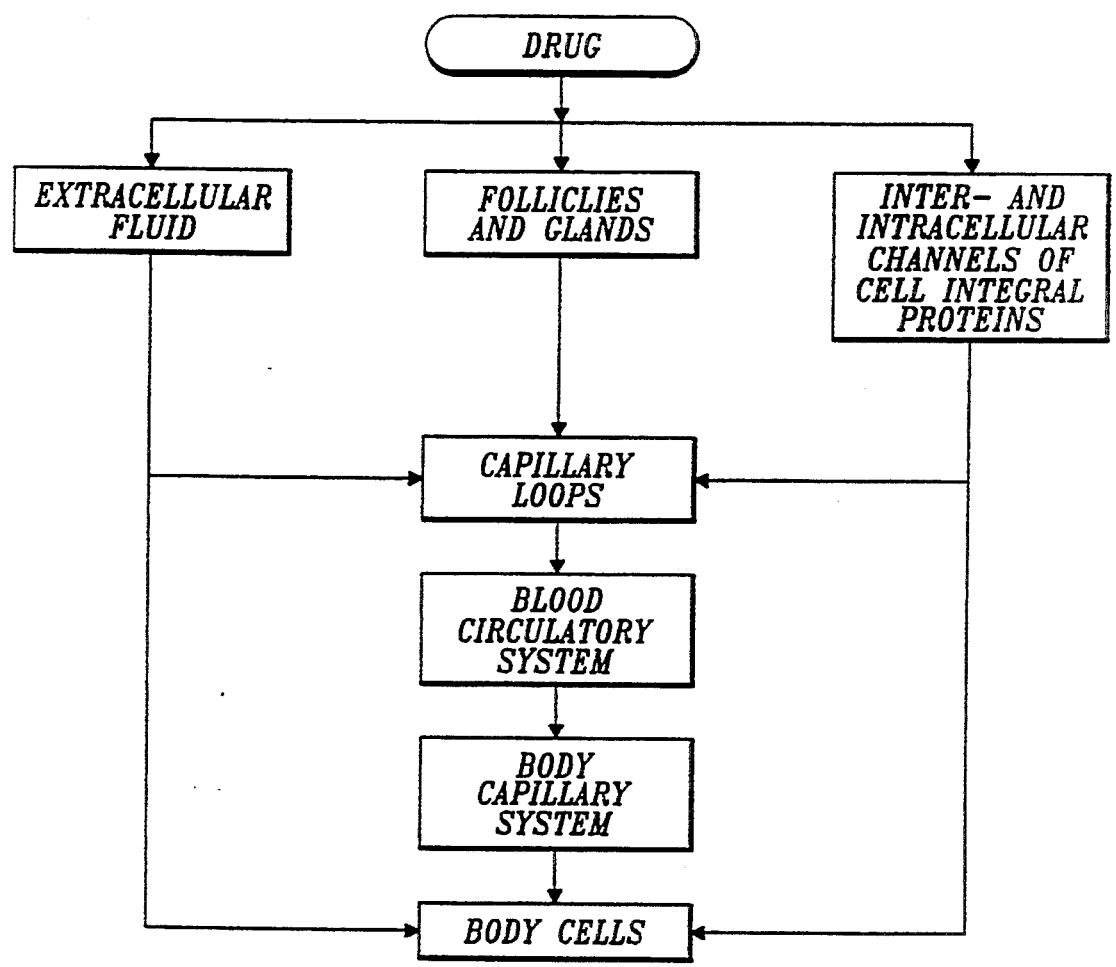
FIG. 4 is a flow diagram illustrating the various paths a drug can take through the skin into the cells of the human body.

The present invention is directed to providing an active transdermal drug delivery system that uses ultrasonic energy to enhance both the movement of drugs and the type of drugs deliverable from a drug reservoir positioned on the surface of the skin to the capillary loops 51 as well as directly to body cells. As shown in FIG. 4, various paths exist for drugs to move from the surface of the skin of an organism such as the human body to the cells of the organism. One path is through the hair follicles and sweat glands to the capillary loops. Another path to the capillary loops is through the extracellular fluid that surrounds body cells. A third path is through the cells, namely, through inter- and intra-cellular channels of cell integral proteins. Drugs entering the capillary loops travel to body cells through the blood circulatory and body capillary systems. In addition, extracellular fluid intra- and inter-cellular channels create direct paths to body cells.

Except in cases of localized therapeutic treatment, the primary path for transdermally administered drugs is through the follicles and glands. The next most significant path is the extracellular fluid path. The slowest or least effective path is through the cells' inter- and intra-cellular channels. In cases of localized therapeutic treatment, the primary path is the extracellular path followed by the follicle and gland path and, then, the inter- and intra-cellular channels.

As will be better understood from the following description, the invention provides an active transdermal drug delivery system that uses ultrasonic waves to first stimulate the skin in a manner that opens (i) the dermal-epidermal junction or basal membrane and (ii) the capillary endothelial cell joints and, then, pumps a stored drug through the skin into the capillary loops. Stimulation is accomplished by applying relatively low frequency (5 KHz–1 MHz) ultrasonic stimulation pulses through the skin for a predetermined period of time (10–20 seconds). Thereafter, higher, variable frequency (50 MHz–300 MHz) pulses are applied obliquely to the skin. The obliquely applied pulses create a pumping action that pumps drugs through the openings created by the stimuli pulses. Some embodiments of the invention also use ultrasonic waves to withdraw body fluids into a chamber to test for substance (drug) concentration. The results of the test are used to control drug delivery. Further, the substance concentration sensor can be used as a stand-alone device.

Figure 5:
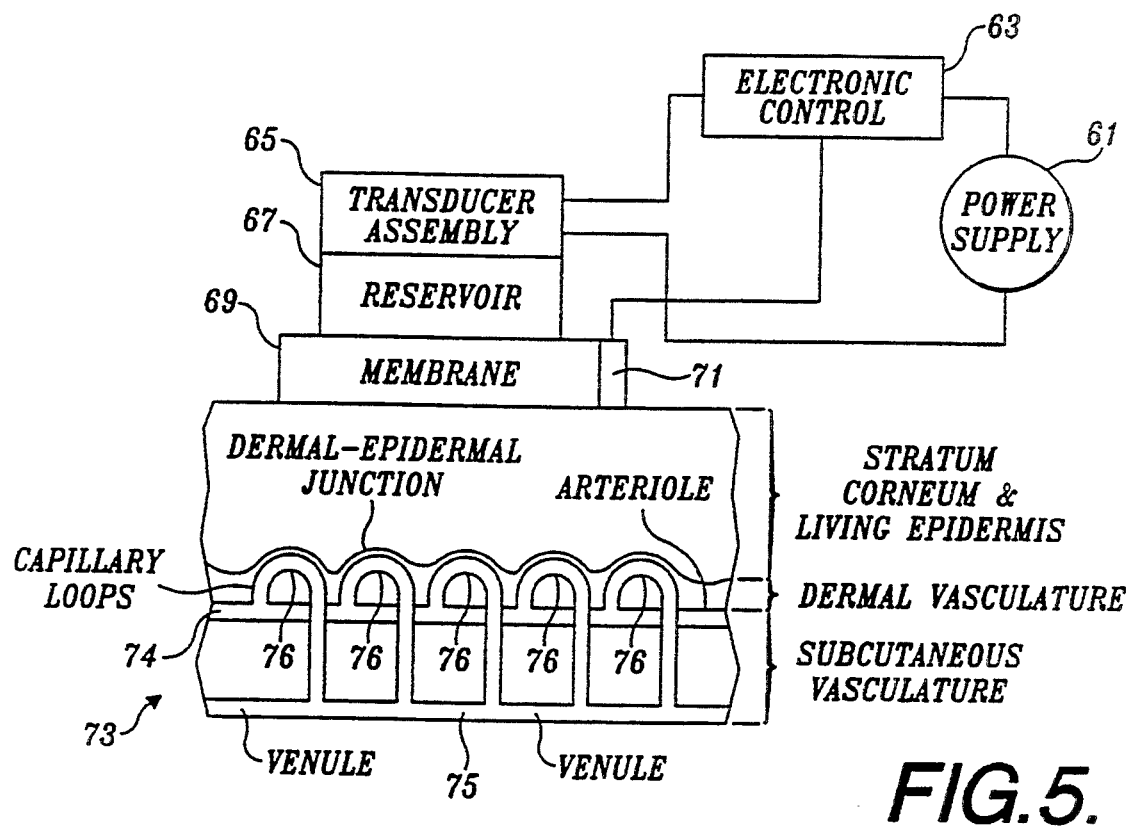
FIG. 5 is a block diagram of an ultrasonic transdermal drug delivery system formed in accordance with the invention.

FIG. 5 is a block diagram illustrating a first embodiment of the invention. The embodiment of the invention illustrated in FIG. 5 includes: a power supply 61; electronic control circuit 63; an ultrasonic transducer assembly 65; a drug reservoir 67; a polymeric membrane 69; and a temperature sensor 71. The polymeric membrane is a polymeric membrane whose porosity is controllable by ultrasonic waves, i.e., the polymeric membrane is an ultrasound controllable polymeric membrane.

Also illustrated in FIG. 5 is a section of skin 73 containing a single arteriole 74, and a single venule 75 joined by a plurality of capillary loops 76. The illustrated arrangement is to be taken as illustrative of the capillary loops and other blood vessels illustrated in FIG. 1 and described above, and not as limiting.

Figure 6:
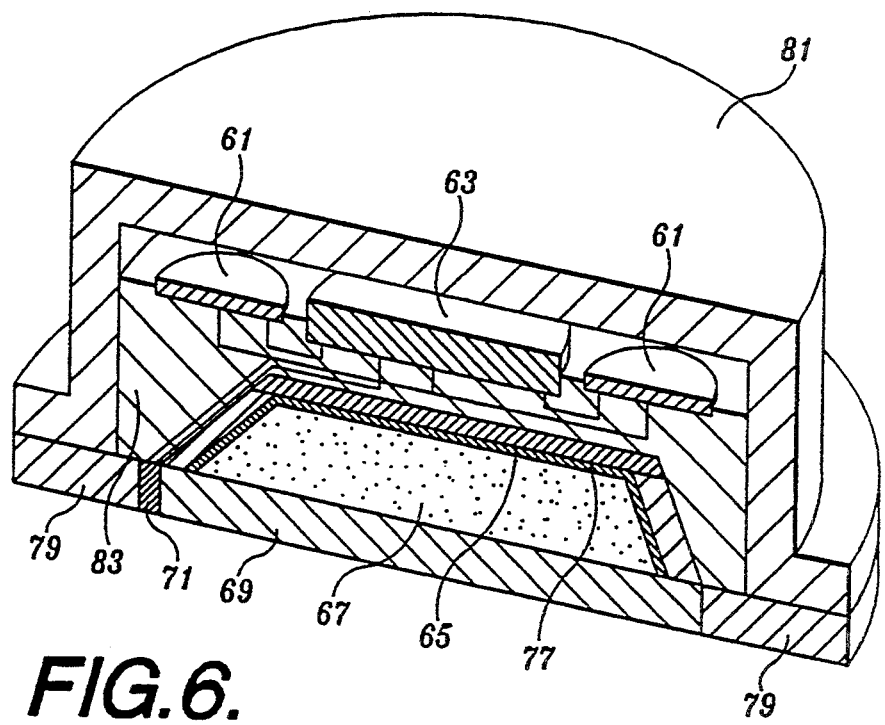
FIG. 6 is a cross-sectional, pictorial view of the structural arrangement of transdermal drug delivery system illustrated in FIG. 3.

As shown, the temperature sensor 71 and polymeric membrane 69 are juxtaposed against the surface of the skin 73. The drug reservoir 67 is located on the opposite side of the polymeric membrane 69. The transducer assembly is located atop the reservoir, or more correctly as shown in FIG. 6 and described below, around the reservoir. The power supply, under the control of the electronic control, supplies power to the ultrasonic transducer assembly. The electronic control is more fully shown in FIG. 9 and described below.

Figure 7:
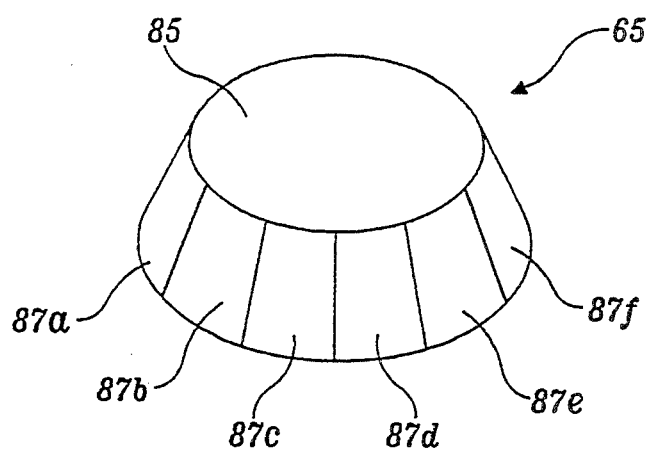
FIG. 7 is a pictorial view of the ultrasonic transducer assembly portion of the transdermal drug delivery system illustrated in FIG. 6.
Figure 8:
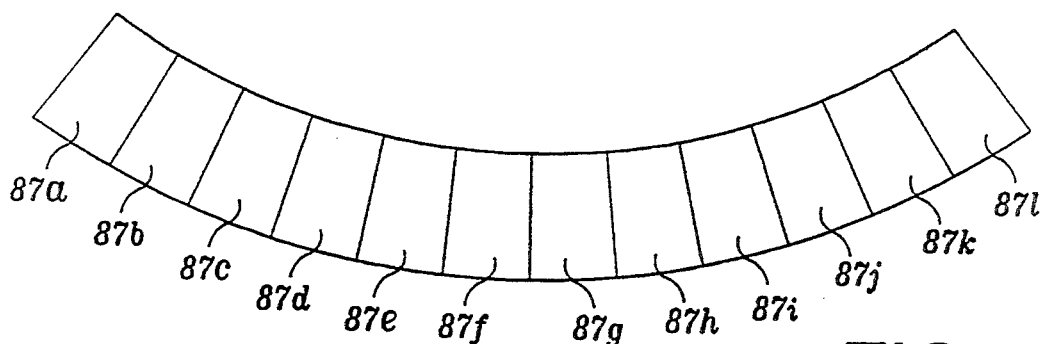
FIG. 8 is a plan view of the transducer segment portion of the ultrasonic transducer assembly illustrated in FIG. 5.

FIG. 6 is a sectional, pictorial view of the structured arrangement of the embodiment of the invention illustrated in FIG. 5 and described above. FIG. 6 illustrates that the drug reservoir 67 has the shape of a truncated cone and that the polymeric membrane 69 is located along the large side of the truncated cone. The transducer assembly 65, which is illustrated in FIGS. 7 and 8 and described below, defines the wall and smaller side of the truncated cone. Located between the transducer assembly 65 and the reservoir 67 is a drug-impermeable laminate 77. The drug-impermeable laminate, in addition to being impermeable to the drug contained in the reservoir 67, also functions as a focusing lens for the transducers that form the transducer assembly 65. In this regard, preferably the drug-impermeable laminate is a Fresnel lens.

Figure 29:
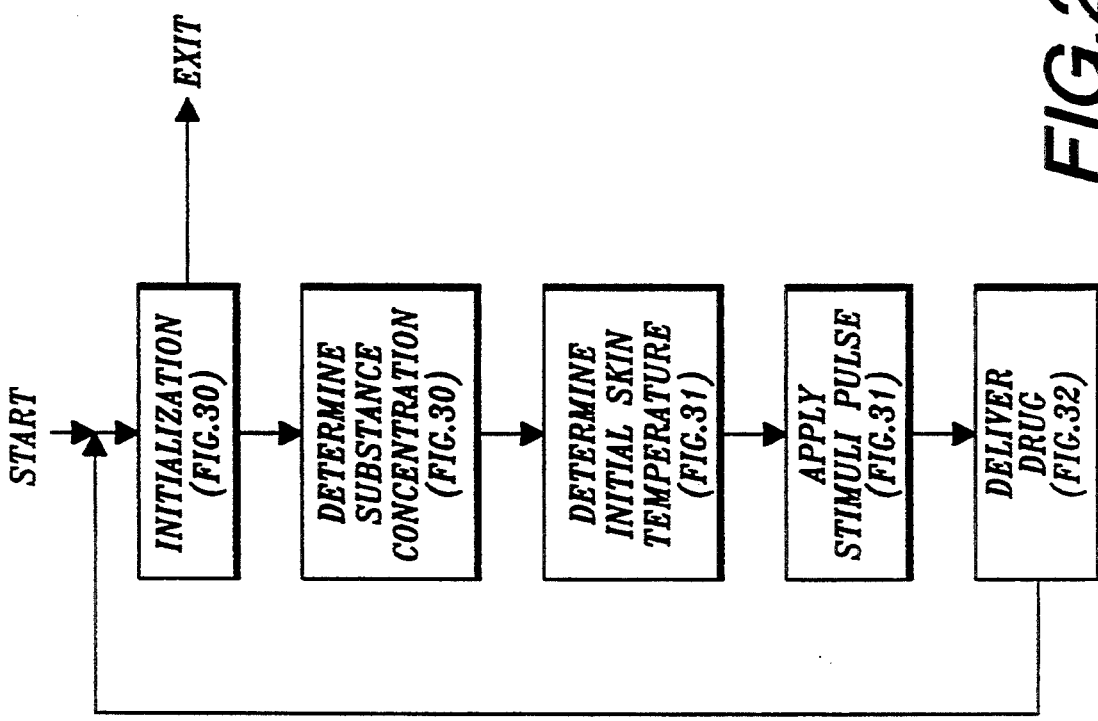
FIG. 29 is a master flow diagram illustrating the operation of the microprocessor of the embodiment of the invention illustrated in FIG. 26.

The temperature sensor 71 is positioned at the edge of the polymeric membrane. Surrounding the polymeric membrane 69 and the temperature sensor 71 is an adhesive film seal 79. The power supply 61, the electronic control 63, the transducer assembly 65 and the remaining components are all mounted in a hat-shaped housing 81. The adhesive seal 79 and the membrane 69 enclose the open end of the hat-shaped housing 61. If desired, encapsulation material 83 can be used to support and encapsulate the power supply 61 and the electronic control circuit 63, and provide support for the transducer assembly 65. As illustrated in FIG. 29 and described below, preferably, the drug-impermeable laminate 77 and the polymeric membrane 69 form a sealed canister that is removably mounted in the hat-shaped housing 81.

As illustrated in FIGS. 7 and 8, the transducer assembly 65 includes a flat, circular transducer 85 that defines the small side of the truncated cone formed by the transducer assembly 65. A plurality of equally sized and equally spaced transducer segments 87a, 87b, 87c, 87d, . . . define the walls of the truncated cone. Preferably, the number of equally sized and equally spaced transducer segments is an even number. While, as shown in FIG. 8, which is a plan view of the transducer segments, the illustrated embodiment of the transducer assembly includes twelve (12) segments, this number should be taken as illustrative, and not limiting. Preferably, the resonant frequency of the flat, circular transducer is lower than the resonant frequency of the transducer segments. For example, the resonant frequency of the flat, circular transducer may be 1 MHz while the resonant frequency of the transducer segments 87a, 87b, 87c, 87d . . . may be 50 MHz.

Figure 9:
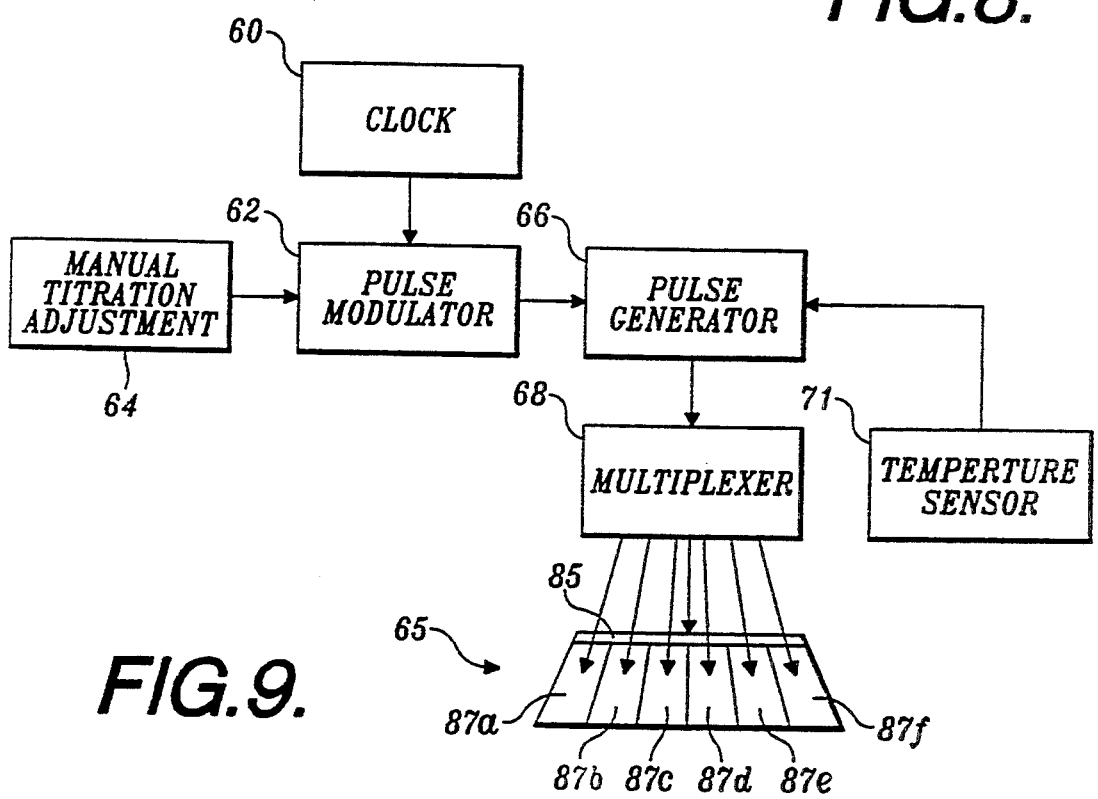
FIG. 9 is a block diagram of the electronic control portion of the ultrasonic transdermal drug delivery system illustrated in FIGS. 5 and 6.

FIG. 9 is a functional block diagram of the electronic control 63. The block diagram includes: a clock 60, a pulse modulator 62, a manual titration adjustment control 64, a pulse generator 66 and an ultrasonic transducer multiplexer 68. FIG. 9 also includes the temperature sensor 71 and the transducer array 65. The clock 60 generates clock pulses at a rate at or above the highest frequency of the pumping pulses to be applied to the transducer segments 87a, 87b, 87c, 87d . . . The pulse modulator 62 divides the clock pulses to a suitable level and produces control pulses that control the operation of the pulse generator 66 so that pulses of suitable amplitude, length (duty cycle) and frequency are applied to the multiplexer as the multiplexer couples the output of the pulse generator to the flat, circular transducers 85 and the transducer segments 87a, 87b, 87d . . . of the transducer assembly in the sequence illustrated in FIG. 10 and described below. For ease of illustration and because circuits for operating multiplexers are well known, the control system for the multiplexer is not shown in FIG. 9.

The manual titration adjustment control is coupled to the pulse modulator and controls the enablement of the pulse modulator in a way that controls the amount of drug delivered from the reservoir to the organism in the manner described below. That is, the manual titration adjustment control controls the ability of the pulse modulator to start a drug delivery cycle and cause the pulse generator to send a sequence of delivery control pulses to the multiplexer and, thus, to the transducers of the transducer assembly 85.

The temperature sensor is connected to the pulse generator and prevents the pulse generator from applying a sequence of delivery pulses to the transducer assembly if the temperature of the skin rises above a predetermined level. Thus, the temperature sensor functions as a safety device.

Figure 10:
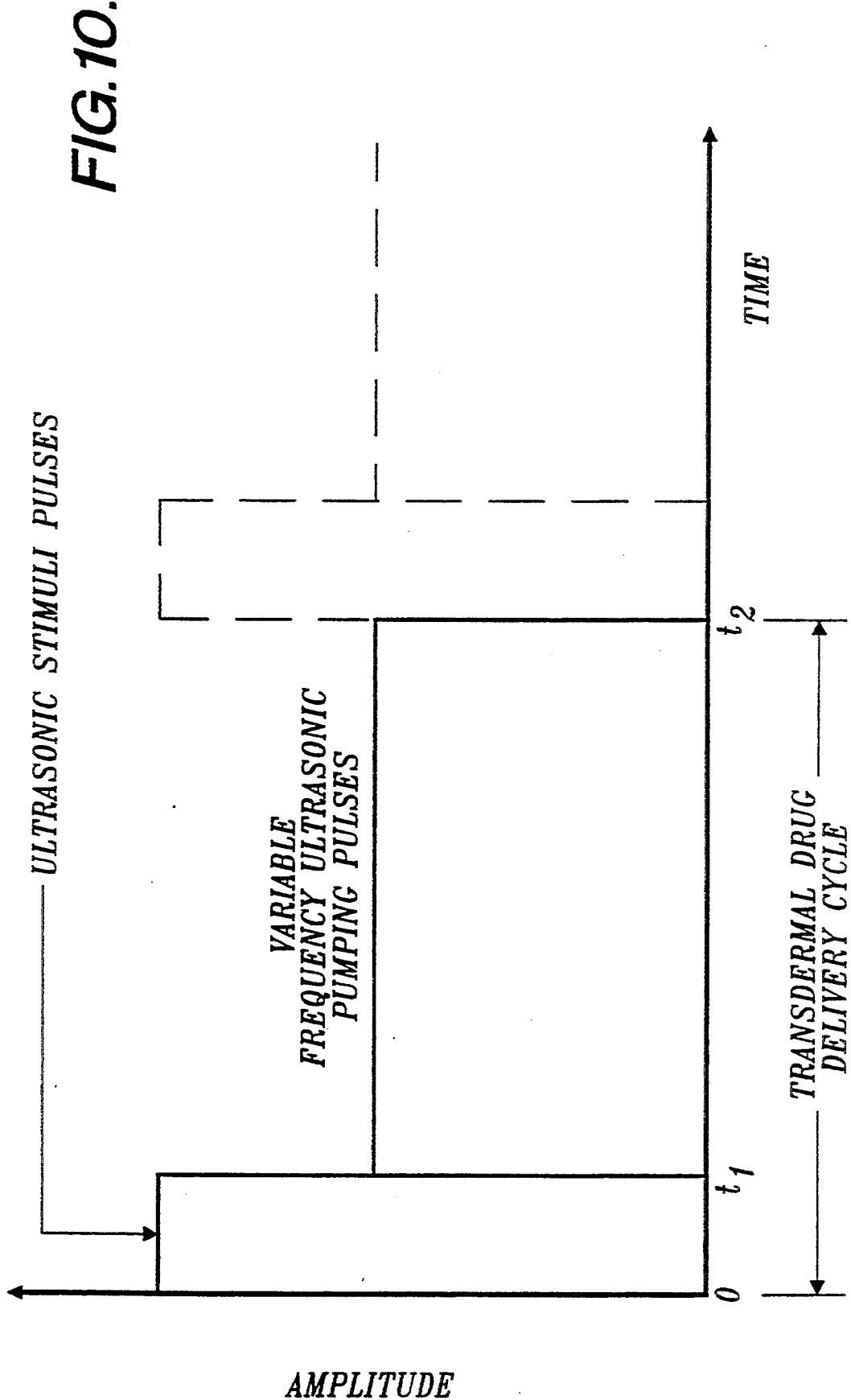
FIG. 10 is a timing diagram illustrating the drug delivery cycle of the ultrasonic transdermal drug delivery system illustrated in FIGS. 5 and 6.

FIG. 10 is a timing diagram illustrating a drug delivery cycle or, more specifically, the sequence of application of ultrasonic pulses to the flat, circular transducer 85 and to the transducer segments 87a, 87b, 87c, 87d . . . As shown in FIG. 10, first, ultrasonic stimuli pulses produced by the pulse generator.66 are applied to the flat, circular transducer 85 by the multiplexer 68. Preferably, the stimuli pulse frequency lies in the 5 KHz-1 MHz range. The ultrasonic stimuli pulses are applied to the flat, circular transducer 85 for a predetermined period of time ($0$–$t_1$) adequate to open the dermal-epidermal junction membrane and the capillary endothelial cell joints. The predetermined period of time is dependent upon the power contained in the stimuli pulses and the time the dermal-epidermal junction membrane and the capillary endothelial cell joints are to be opened, i.e., how long it takes for the skin to return to normal. For example, the application of 1 MHz pulses containing about 0.2 watts for about 20 seconds will result in the dermal-epidermal junction and the endothelial cell joints remaining open for about five minutes. The application of 1 MHz pulses containing 0.3 watts of power for 20 seconds will result in the dermal-epidermal junction membrane and the capillary endothelial cell joints remaining open for approximately 20 minutes. Applying the same frequency and power stimulation pulses for a significantly longer period of time does not significantly extend the opening time. Conversely, increasing the power to 3 watts (which is unacceptably high) at the same frequency (1 MHz) for 20 seconds increases the opening period to over 30 minutes.

Between ultrasonic stimuli pulse periods (i.e., during time $t_1$–$t_2$), higher, variable frequency ultrasonic pumping pulses are applied to the ultrasonic transducer segments 87a, 87b, 87c, 87d . . . The variable frequency, ultrasonic pulses, which are produced by the pulse generator 66, are applied to pairs of opposing transducer segments in a rotating manner by the multiplexer 68. More specifically, a sequence of variable frequencies is first applied to one pair of opposed transducer segments. The preferred initial pumping pulse frequency is the resonant frequency of the segments—50 MHz, for example. After the resonant frequency is applied for a period of time, pulses at the second and then the third harmonic (100 MHz and 150 MHz) are sequentially applied for a predetermined period of time. If desired, pulse trains at the fourth, fifth and sixth harmonics can be sequentially applied thereafter. After a harmonic sequence has been applied to one pair of opposed transducer segments, the cycle is repeated with the next adjacent pair of opposed transducer segments in one direction or the other, i.e., clockwise or counterclockwise. That is, first a train of pulses at the resonant or fundamental frequency is applied to the next pair of opposed transducer segments followed by trains of pulses at the first harmonic, second harmonic, etc. Pulses are continuously applied in this rotating manner until the transdermal drug delivery cycle ends. A resonant or fundamental frequency of around 50 MHz is important because the wave length of a 50 MHz signal is approximately twice the distance between body cells. As a result, the pumping energy moves the cells receiving the energy approximately one cell distance. As will be better understood from the following discussion, it is the pumping motion of the body cells that, in part, moves the drug stored in the reservoir through various skin pathways into the bloodstream. After $t_2$, the cycle is repeated, unless inhibited by the temperature sensor.

Figure 11:
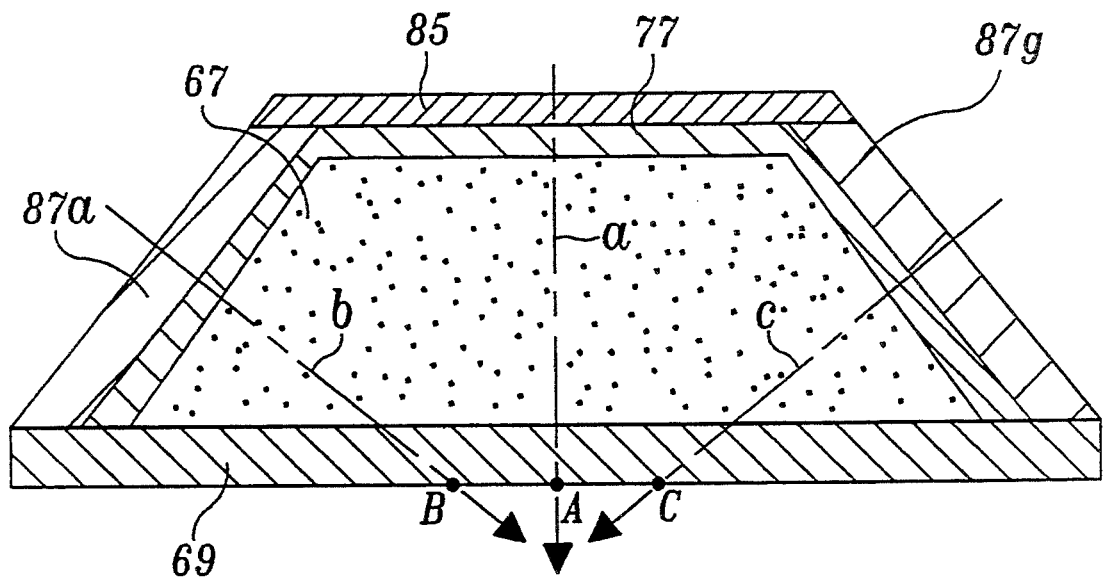
FIG. 11 is a cross-sectional view of the ultrasonic transducer assembly illustrated in FIG. 7 and the drug reservoir enclosed by the assembly.
Figure 12:
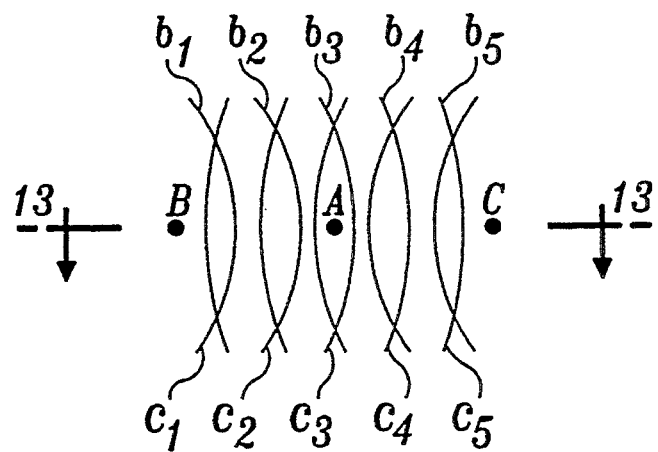
FIG. 12 is a plan view showing the movement of waves across the surface of the skin produced by the ultrasonic transducer assembly illustrated in FIG. 11.
Figure 13:
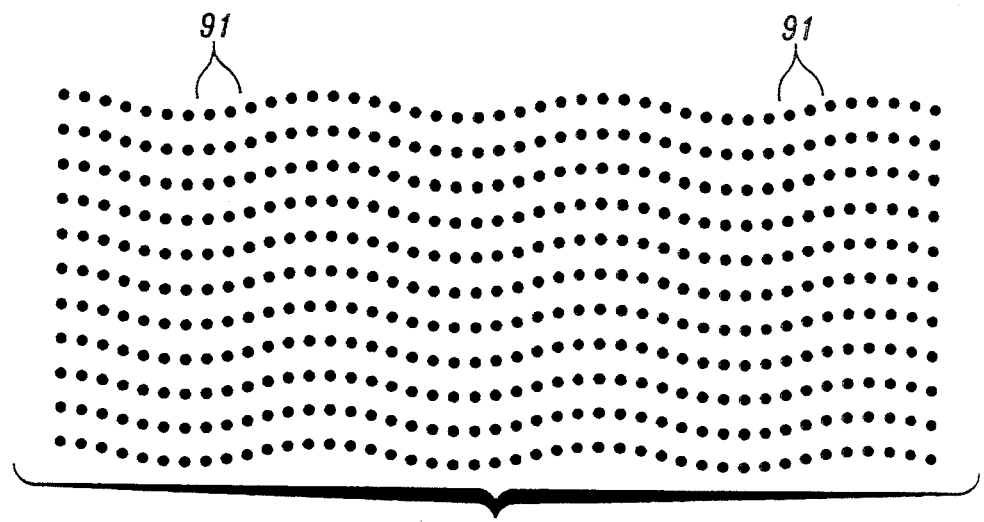
FIG. 13 is a pictorial cell diagram illustrating the effect of applying an ultrasonic transducer signal perpendicularly to the skin.

FIGS. 11–13 illustrate further the operation of the invention. As noted above, initially, ultrasonic stimuli pulses are applied to the flat, circular ultrasonic transducer 85 for a predetermined period of time. Since the flat, circular ultrasonic transducer 85 lies parallel to the skin, the stimuli pulses travel along axis a and impinge on the skin perpendicularly hitting first at point A. As noted above, the stimuli pulses open the dermal-epidermal junction membrane and the capillary endothelial cell joints. After the stimuli pulses have been applied for an adequate period of time, the higher, variable frequency ultrasonic pulses are applied to pairs of opposed transducer segments in a rotating manner, as described above. Because the transducer segments are angled with respect to the surface of the skin, ultrasonic waves produced by the pairs of transducer segments 87a through 87g impinge on the skin at an oblique angle, depicted by lines b and c in FIG. 11. Impingement is centered at points B and C, respectively. The higher, variable frequency ultrasonic pulses create opposing moving waves in the skin. Ultrasonic waves impinging at point B create skin waves b1, b2, b3, b4 . . . that move toward point C and ultrasonic waves impinging at point C create skin waves c1, c2, c3, c4 . . . that move toward point B. The resulting waves cause a pumping action that moves the drug located in the reservoir 67 first through the polymeric membrane 69 and then through the skin into the blood vessels. The angle of inclination of the transducer segments in combination with the focal length of the Fresnel lens formed by the drug-impermeable laminate 77 positioned in front of the transducer segment can be adjusted to achieve a desired depth of penetration. The greater the oblique angle formed by axes b and c with respect to the underlying skin, the deeper the penetration of the ultrasonic waves.

Figure 14:
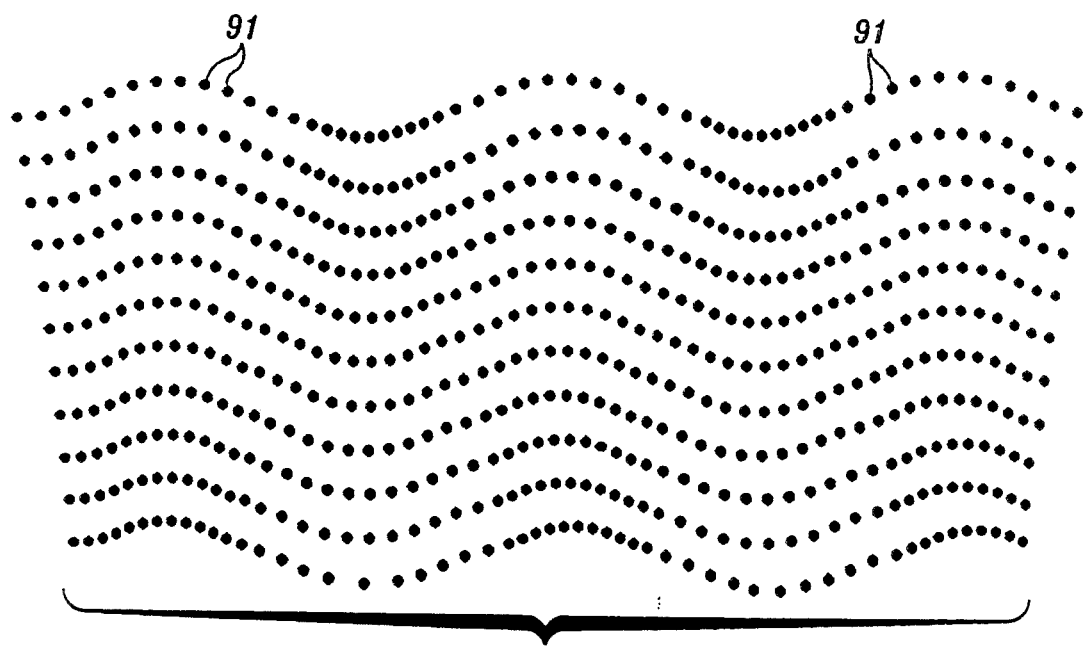
FIG. 14 is a pictorial cell diagram illustrating the effect of applying an ultrasonic transducer signal to the skin at an oblique angle.

FIGS. 13 and 14 illustrate the pumping action that occurs when ultrasonic waves are applied to the skin both vertically and at an oblique angle as illustrated in FIG. 11 and described above. More specifically, FIG. 13 illustrates a plurality of skin cells 91 and the type of skin wave that is created when a suitable frequency ultrasonic pulse is applied perpendicularly to the skin. As can be seen, the cells all remain generally equally spaced as the wave moves through the skin.

FIG. 14 illustrates what occurs when a suitable frequency ultrasonic wave impinges on the skin at an angle. When this occurs, the space in between the cells 91 varies as the wave passes through the skin. Initially, the spacing between some of the cells at the skin surface becomes larger than normal and between others becomes closer than normal. The larger than normal openings receive the drug to be delivered to the bloodstream. As the wave moves, the spacing between lower skin cells becomes greater while the spacing between higher skin cells becomes closer. This increase and decrease in spacing creates a "pumping" action that moves a drug positioned on the surface of the skin through the skin to the underlying cells and blood vessels. The pumping action occurs not only to the skin cells. A similar pumping action occurs along the walls of the hair follicle channels and the sweat glands which, as noted above, creates additional passageways into the blood vessels. Because the space between the cells is increased and decreased, drug molecules larger than in the past can be moved through the skin into the blood vessels. Because the fundamental pumping frequency is chosen to equal one-half the spacing between skin cells, the system is highly efficient. That is, the greatest cellular movement for the energy applied occurs because one-half of the wavelength of the applied ultrasonic energy equals the spacing between the cells being moved. Both higher and lower frequencies are less efficient. Efficiency of movement through the channels around hair follicles is high because of the angular orientation (FIGS. 2 and 3) of hair follicles.

As best understood, the ultrasonic stimuli pulses create the same effect as skin trauma, i.e., a blow to the skin or the application of heat to the skin. In the case of an injury, the trauma causes the basal membrane and the capillary system to open and fluids to flow to the injured area of the skin. The ultrasonic pulses create the same type of opening. The present invention takes advantage of the "gates" that are opened to pump drugs through the skin into the blood stream of the organism. Because of the nervous system (and/or local tissue reaction) the skin rapidly learns that no trauma has occurred and, thus, closes the "gates" after 15–20 minutes (or more), depending upon the magnitude of the applied energy, as shown in FIG. 10, ultrasonic stimuli pulses must be reapplied. As noted above, the preferred frequency of the ultrasonic stimuli pulses lie in the 5 KHz–1 MHz range.

Figure 15:
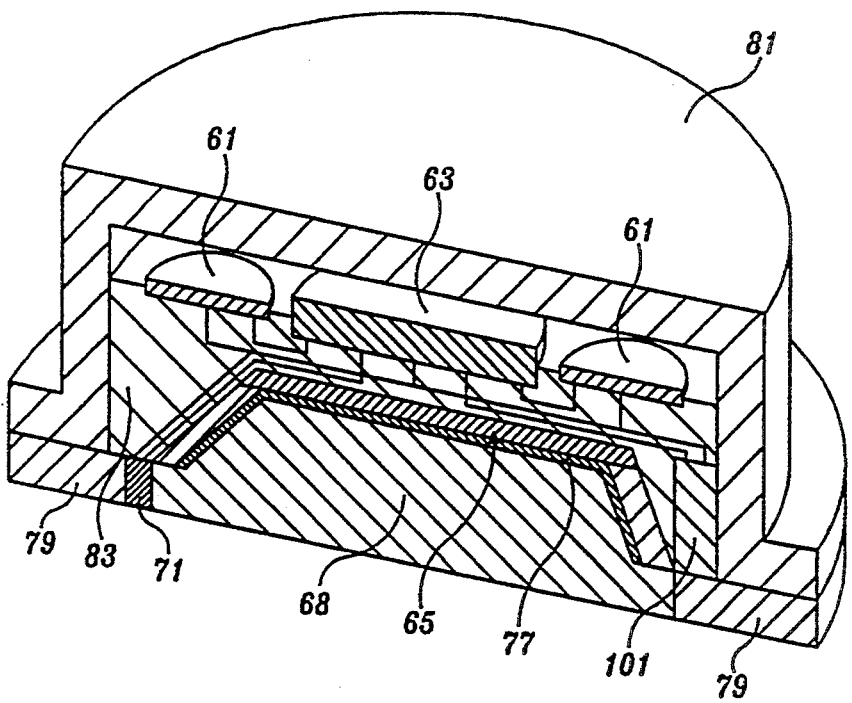
FIG. 15 is a cross-sectional, pictorial view of the structural arrangement of an alternative embodiment of an ultrasonic transdermal drug delivery system formed in accordance with the invention.
Figure 16:
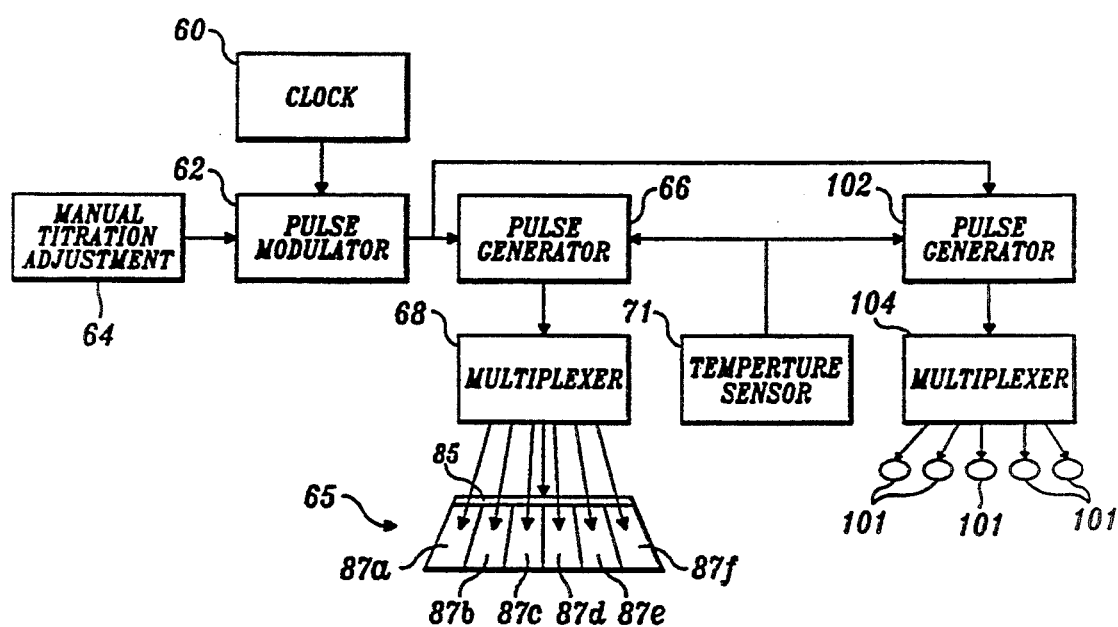
FIG. 16 is a block diagram of the electronic control portion of the ultrasonic transdermal drug delivery system illustrated in FIG. 15.

FIGS. 15 and 16 illustrate an alternative embodiment of the invention. Since the embodiment of the invention illustrated in FIGS. 15 and 16 is generally similar to the embodiment of the invention illustrated in FIGS. 5–9, similar elements, which are identified by the same reference numerals, are not further described except with respect to their interaction with additional elements.

The primary difference between the embodiment of the invention illustrated in FIGS. 5–9 and the embodiment of the invention illustrated in FIGS. 15 and 16 is the addition of one or more infrared (IR) or laser emitters 101. As shown in FIG. 15, the IR or laser emitters 101 are connected to the control electronics. As shown in FIG. 16, the control electronics is modified to include an additional pulse generator 102 and, if more than one IR or laser emitter 101 is included, a multiplexer 104. Like the pulse generator 66 connected to the planar, circular ultrasonic transducer 85 and the transducer segments 87a, 87b, 87c, 87d . . . of the transducer assembly 65, the additional pulse generator 102 is controlled by the pulse modulator 62. The output of the additional pulse generator 102 is connected via the additional multiplexer 104 to the IR or laser emitters 101. As before, the control electronics for the multiplexer 104 are not illustrated because multiplexer control electronics are well known. Rather, the multiplexer timing is shown in FIG. 17 and described below.

The temperature sensor 71 is also connected to the additional pulse generator 102 to limit the application of energy to the IR or laser emitters 101. This limiting connection is important because in this version of the invention the majority of the heat generated in the skin is created by the IR or laser emitters, rather than by the ultrasonic transducers.

Figure 17:
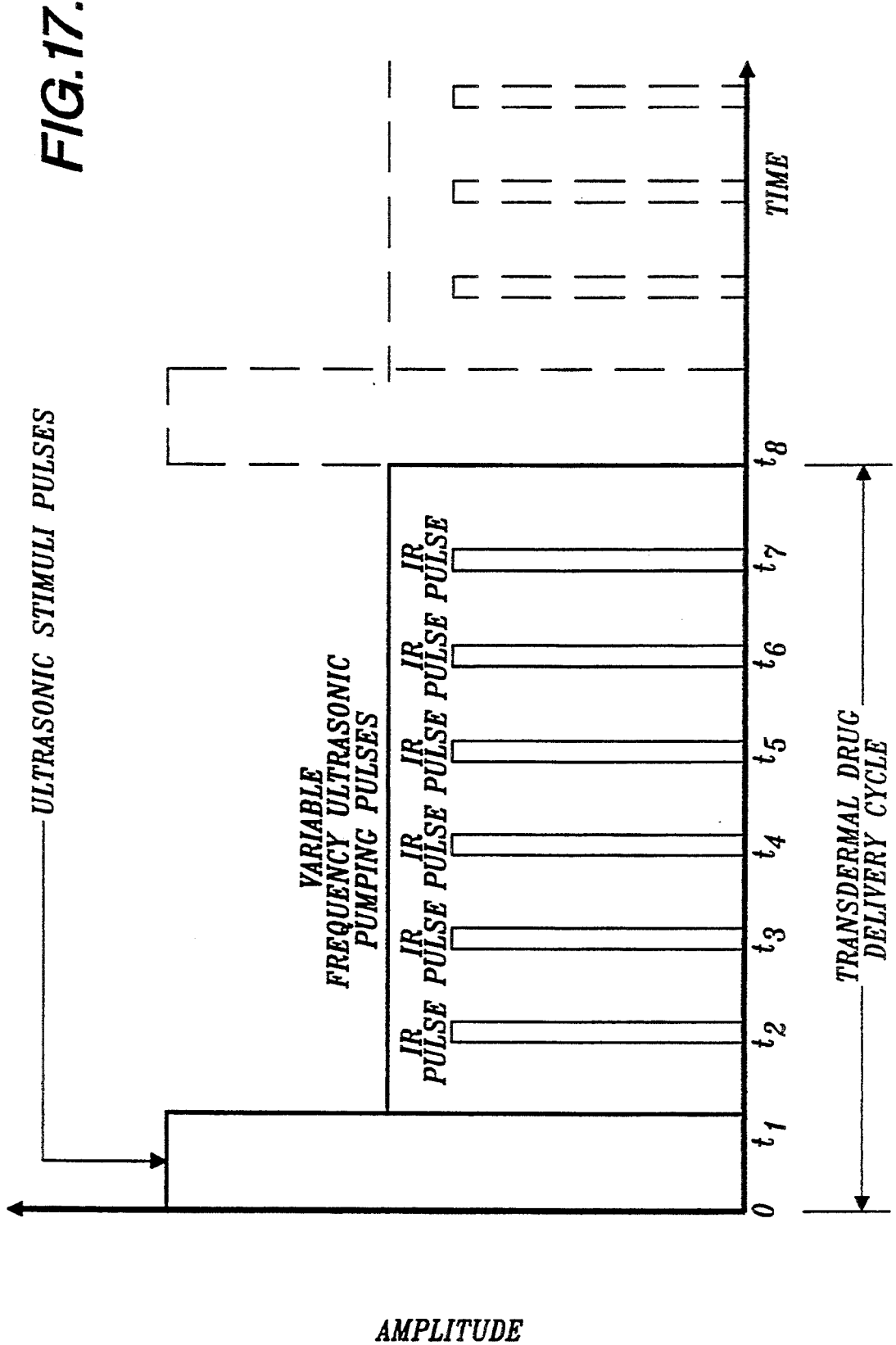
FIG. 17 is a timing diagram illustrating the drug delivery cycle of the ultrasonic transdermal drug delivery system illustrated in FIG. 15.

As shown in FIG. 17, the IR or laser emitters 101 emit pulses at regular intervals during the period of time that variable frequency, ultrasonic pumping pulses are being applied to the skin by the transducer segments 87a, 87b, 87c, 87d . . . in the manner heretofore described. The IR or laser emitter pulses improve the operation of the invention. As best understood, the IR or laser emitter pulses improve the operation of the invention by increasing blood flow similar to the way exercise creates blood flow. This causes the drug being delivered to dissipate faster through the body. The IR or laser emitter pulses also generate heat in the skin as well as create a shock wave similar to the shock wave created by a blow to the skin. It has been found that some IR frequencies are better than others. The best frequencies fall in the following ranges: 500–800 nm (nanometers); 1500–1700 nm; 2100–2300 nm; 3600–4100 nm; and 10,000–10,900 nm.

FIG. 15 also illustrates that the reservoir 67 and the ultrasound controllable polymeric membrane 69 can be combined into a single unit 68. The single unit 68 is also an ultrasound controllable polymeric membrane that holds the pharmaceutical to be delivered, as well as controls the release of the pharmaceutical. A single-layer polymer or a multiple-layer polymer with different ultrasound controlled characteristics can be used. In the latter case, one of the polymers forms the reservoir and the other prevents the reservoir from releasing or oozing in the absence of ultrasound of a suitable frequency.

Figure 18:
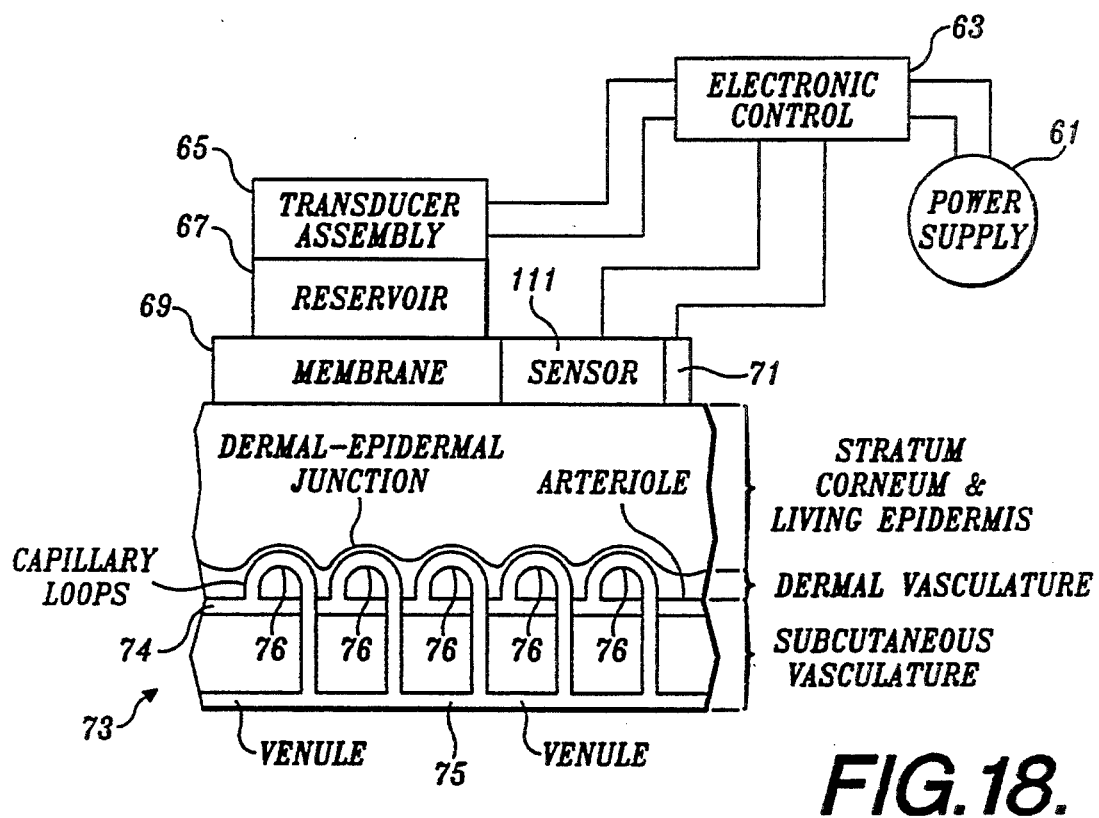
FIG. 18 is a block diagram of another alternative embodiment of an ultrasonic transdermal drug delivery system formed in accordance with the invention.
Figure 19:
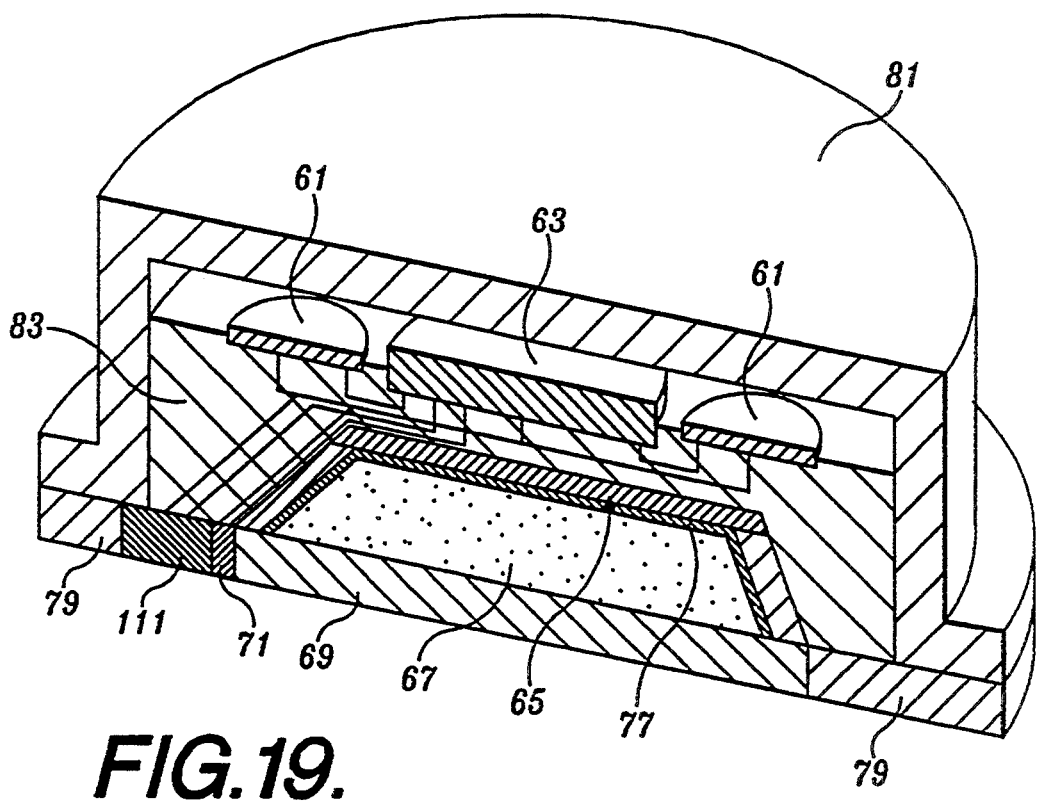
FIG. 19 is a cross-sectional, pictorial view of the structural arrangement of the embodiment of the invention illustrated in FIG. 18.
Figure 20:
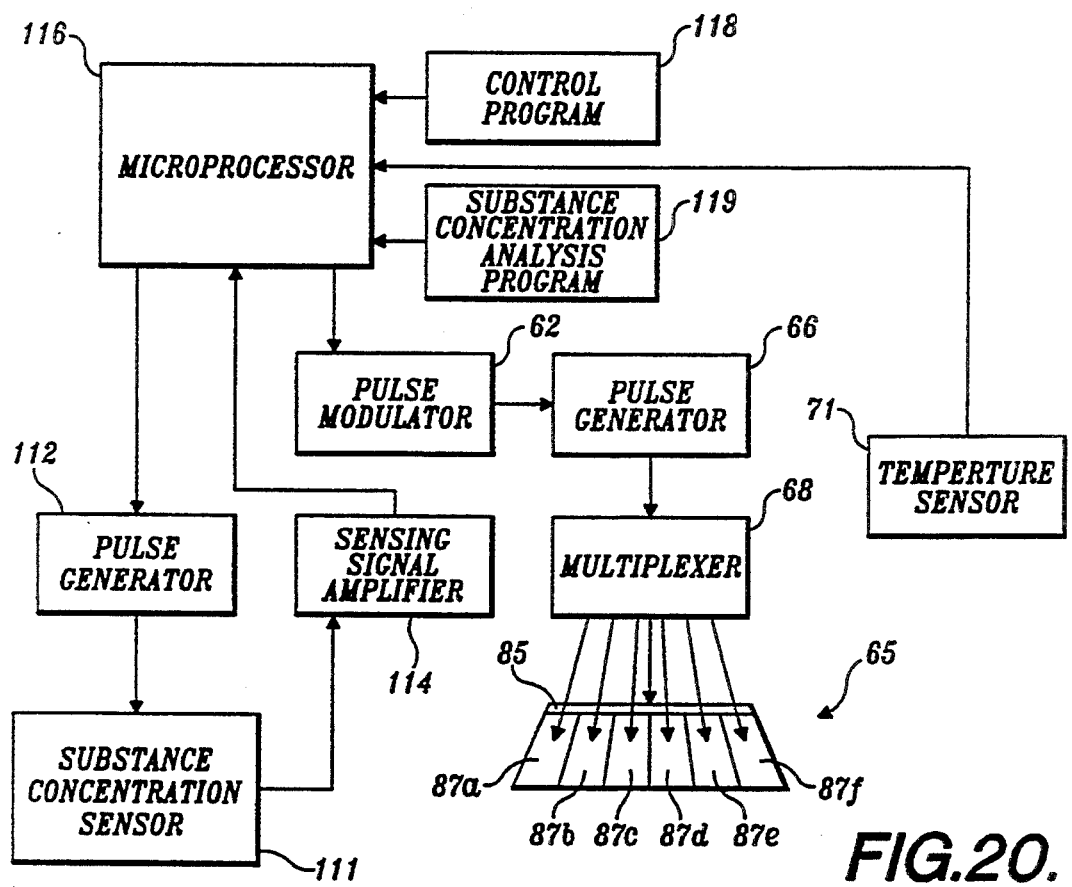
FIG. 20 is a block diagram of the electronic control portion of the ultrasonic transdermal drug delivery system illustrated in FIGS. 18 and 19.

FIGS. 18–20 illustrate another alternative embodiment of the invention. The alternative embodiment of the invention illustrated in FIGS. 18–20 is similar to the embodiment of the invention illustrated in FIGS. 5–9. As a result, as with the FIGS. 15 and 16 embodiment of the invention, similar reference numerals are used with similar components and previously described components are not further described. The primary difference between the embodiment of the invention illustrated in FIGS. 5–9 and the embodiment of the invention illustrated in FIGS. 18–20 is the addition of a substance concentration sensor 111 designed to determine drug effectiveness. As illustrated in FIG. 18, the drug effectiveness sensor supplies a drug effectiveness signal to the electronic control 63.

As illustrated in FIG. 19, the substance concentration sensor 111 is positioned adjacent to the periphery of the polymeric membrane 69. Alternatively, the drug effectiveness sensor could be located remotely from the drug delivery system. In any event, the substance concentration sensor 111 withdraws fluid (serum) from the skin, preferably using the ultrasonic transducer mechanism illustrated in FIG. 22 and described below. The removed fluid is analyzed to determine the effectiveness of the drug delivery system. The result of the analysis is used by the electronic control 63 to control the operation of the transducer assembly 65 and, thus, the delivery of the drug stored in the reservoir 67 to the blood vessel 75.

As shown in FIG. 20, in addition to the inclusion of a substance concentration sensor 111, the electronic control 63 is modified. Rather than including a simple clock/pulse generating mechanism, the electronic control system includes a microprocessor 116 controlled by a control program 118 stored in a suitable memory, such as a read-only memory (ROM). The microprocessor controls the pulse modulator 62, which in turn controls the rate and nature of pulses produced by the pulse generator 66 that are applied to the transducers of the transducer assembly 65 via the multiplexer 68. The microprocessor also controls the operation of a second pulse generator 112, which applies drive pulses to a transducer that forms part of the substance concentration sensor 111. The output of a substance sensing transducer that also forms part of the hereinafter described (FIG. 22) substance concentration sensor 111 is applied to the microprocessor 116 via a sensing signal amplifier 114. A drug concentration analysis program 119 controls the operation of the microprocessor 116 during the substance concentration determination portion of the overall cycle of operation.

Figure 22:
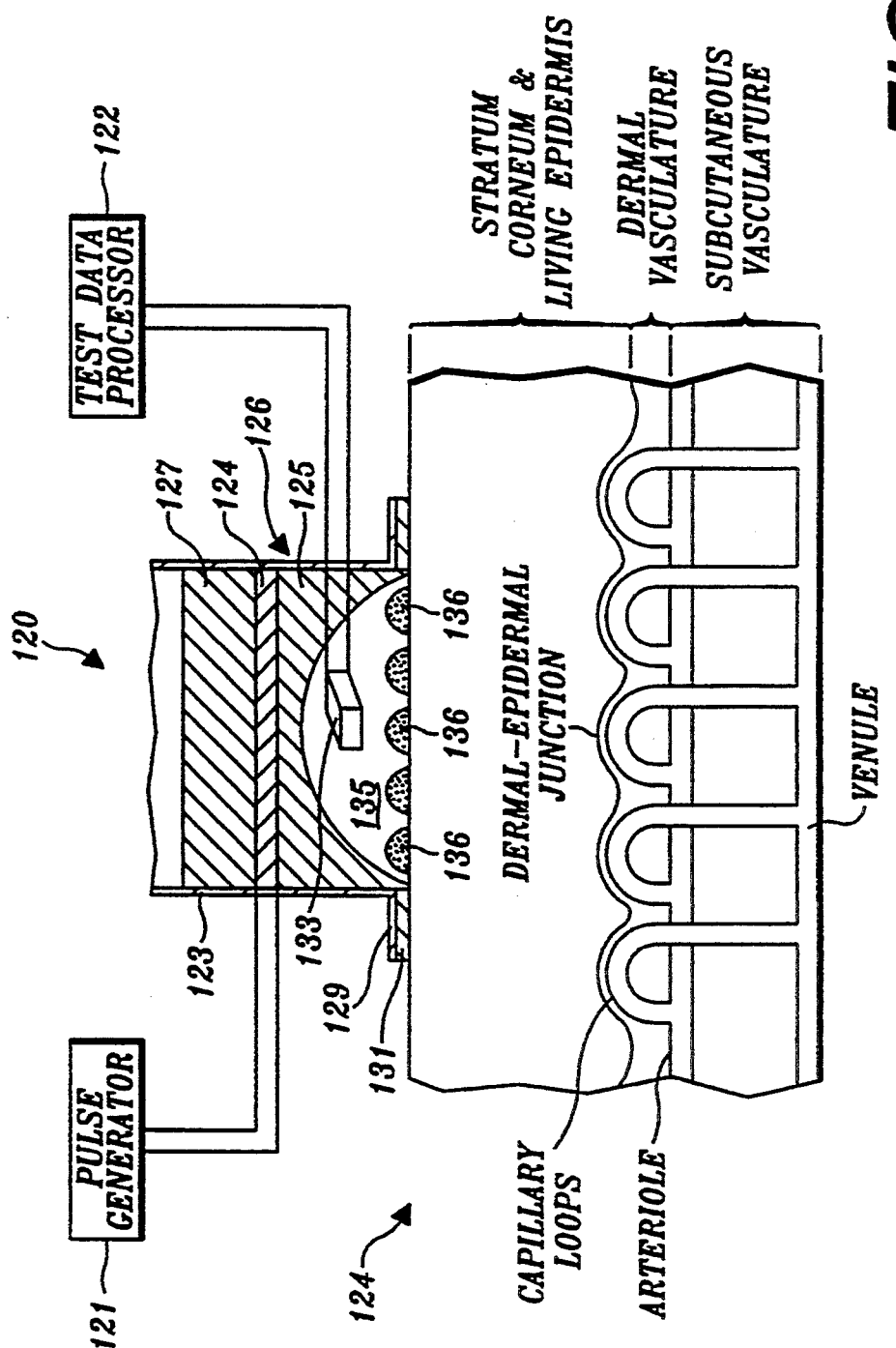
FIG. 22 is a partially pictorial, partially block diagram of a substance concentration sensor formed in accordance with this invention.

In operation, as will be better understood from the following description of the substance concentration sensor illustrated in FIG. 22, the second pulse generator 112 produces pulses that cause an ultrasonic transducer included in the substance concentration sensor 111 to cause fluid to flow into a cavity in the substance concentration sensor 111. A suitable substance sensing transducer, which may take the form of a diffusion cell, a piezoelectric sensor, a pyroelectric sensor, or an ISFET sensor that forms part of the substance concentration sensor 111, determines the concentration of a predetermined substance in the fluid. The results of the determination, after being amplified by the sensing signal amplifier 114, are analyzed by the microprocessor 116 in accordance with drug analysis program 119. The results of the analysis are used to control the delivery character of drugs via the pulse modulator 62, the pulse generator 66, the multiplexer 68 and the transducer assembly 65 in the manner heretofore described. The output of the temperature sensor 71 is utilized by the microprocessor 116 to limit the rate of drug delivery in the event skin temperature exceeds a predetermined level.

Figure 21:
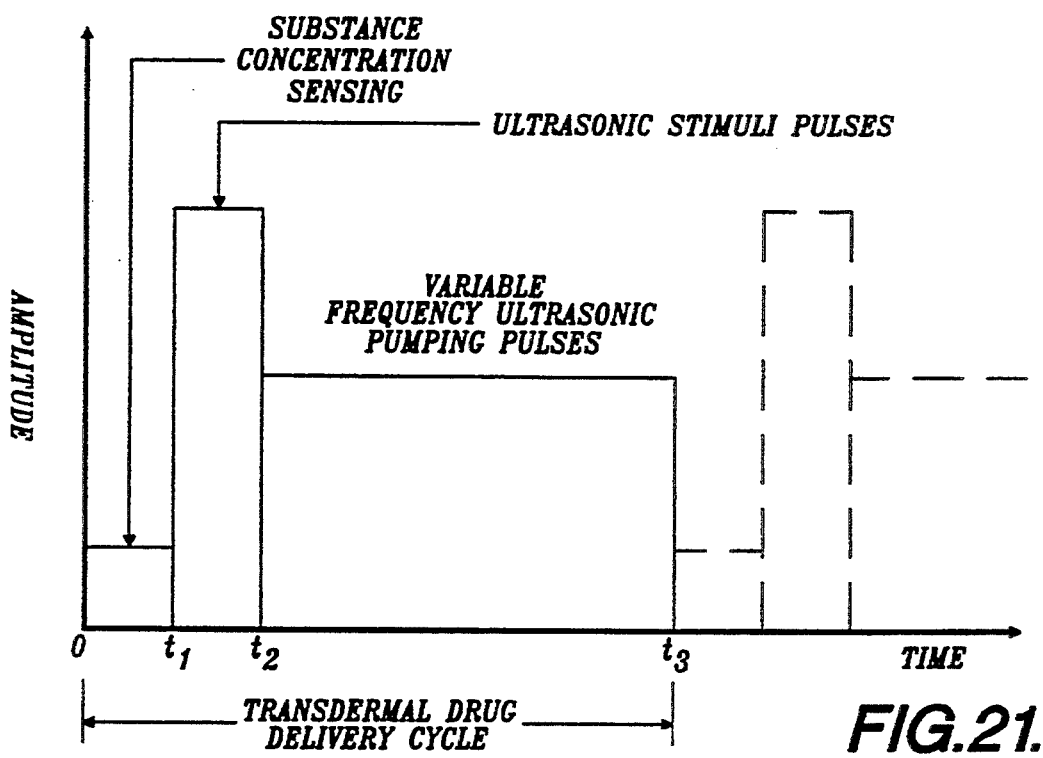
FIG. 21 is a timing diagram illustrating the drug delivery cycle of the embodiment of the invention illustrated in FIGS. 18 and 19.

FIG. 21 is a timing diagram of the drug delivery cycle of the embodiment of the invention illustrated in FIGS. 18-20. As shown in FIG. 21, at the beginning of each drug delivery cycle ($0-t_1$), the substance concentration sensor 111 is activated and the microprocessor analyzes substance concentration in accordance with the drug concentration analysis program 119. Thereafter, in the manner heretofore described, ultrasonic stimuli pulses are produced by the flat, circular, ultrasonic transducer 85 ($t_1-t_2$). As noted above, the stimuli pulses simulate "skin trauma" that causes the basal membrane and capillary endothelial cell joints to open. Then, variable frequency, ultrasonic pumping pulses are produced by opposed pairs of transducer segments 87a, 87b, 87c, 87d . . . in a rotating manner ($t_2-t_3$). The variable frequency, ultrasonic pumping pulses produced by the transducer segments cause the drug to move from the reservoir 67 through the polymeric membrane 69 and the skin 73 into the systemic circulation system. Thereafter, the cycle is repeated.

FIG. 22 illustrates a stand-alone substance concentration sensor 120 formed in accordance with the invention. While illustrated as a stand-alone device, the concentration sensor shown in FIG. 22 is suitable for use in the embodiment of the invention illustrated in FIGS. 18-20. In addition to the substance concentration sensor 120, FIG. 22 includes a pulse generator 121 and a data processor 122. The substance concentration sensor 120 is shown positioned on a section of skin 124.

The substance concentration sensor 120 illustrated in FIG. 22 includes an extraction transducer 126 and a substance sensing transducer 133. The extraction transducer includes a container 123; a planar piezoelectric (ultrasonic) transducer 124; a focusing lens 125; and a backing layer 127. The container is preferably hat shaped and includes, at the bottom, a flange 129 that is attached to the skin 124 of an organism by an adhesive film seal 131. When implemented in a drug delivery system of the type shown in FIGS. 18-20, the container can be eliminated, if desired.

The focusing lens 125 has a plano concave shape oriented such that the concave side faces the skin 124 of the organism. Thus, the focusing lens 125 defines a cavity 135. Located in the cavity 135 is the substance sensing transducer 133. Positioned above the focusing lens is the ultrasonic transducer 124. Positioned above the ultrasonic transducer 124 is the backing layer 127. The pulse generator 121 is connected to and drives the ultrasonic transducer. The data processor is connected to the substance sensing transducer 133.

In operation, the ultrasonic transducer pulses are focused by the focusing lens 125 into the organism and traumatize the skin underlying the cavity 135. The trauma causes the dermal-epidermal junction membrane and the capillary endothelial joints to open and allow fluid 136 to be drawn into the cavity 135. The fluid 136 is sensed by the substance sensing transducer 133, causing the output of the transducer to change. The output changes are analyzed by the data processor 122.

A substance concentration sensor of the type illustrated in FIG. 22 preferably has a skin sample extractor area of about 3.5 $cm^2$. Preferably, the sensor is attached to the arm of a person so as not to interfere with arm articulation. The stratum corneum layer of the epidermis does not have to be striped.

The maximum extraction depth created by the negative radiation pressure produced by the substance sensing transducer depends on a variety of factors. The thickness of all layers between the transducer and the subcutaneous layer and the ratio of all layer thicknesses are important factors. The location of the lens focal plane with respect to the lens face is another factor related to maximum extraction depth, as is the frequency of the ultrasonic wave. The presently preferred frequency range is 3 MHz–50 MHz. The ratio of the speed of sound in sequentially coupled layers and the acoustic impedance of the layers are other important factors. The rate of dilation of the capillary system and intracellular micro circulation tree are other factors. In general, ultrasonic wave propagation will start from the layer having higher density and flow into the media laving a lower density. Based on this knowledge, the extraction transducer 126 should be constructed so that the focal point of the focal lens is positioned at a higher density skin layer level rather than a lower density skin layer level.

Figure 23:
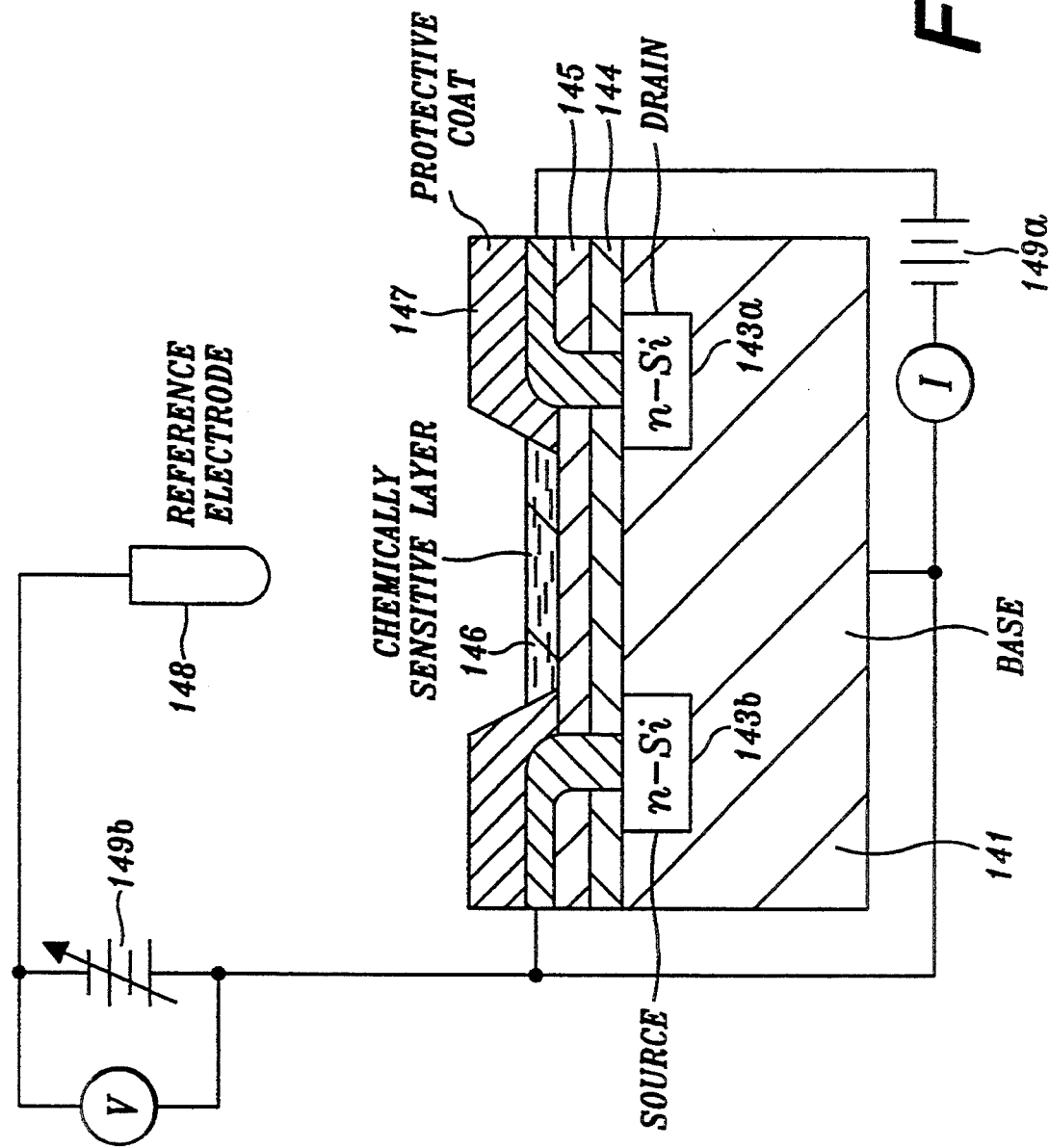
FIG. 23 is a partially pictorial, partially schematic diagram of a substance sensing transducer suitable for use in the substance concentration sensor illustrated in FIG. 23.

FIG. 23 is a partially pictorial, partially schematic diagram of a substance sensing transducer circuit wherein the transducer element is an ISFET (ion sensitive field effect transistor) sensor 140. One source of such sensors is Sentron, Inc., Federal Way, Washington. In general, shown in FIG. 23, an ISFET sensor 140 includes a base 141 formed of p-type silicon, and source and drain regions 143a and 143b formed of n-type silicon embedded in the base. Overlying the base and the source and drain regions is an insulating layer of silicon oxide ($Si\ O_2$) 144. Overlying the silicon oxide layer is a layer of silicon nitride ($Si_3\ N_4$) 145. A chemically sensitive layer 146, surrounded by a protective coating, overlies the silicon nitride layer 147. Aligned with the chemically sensitive layer is a reference electrode 148.

The reference electrode creates a conduction gate when the ISFET sensor 140 is suitably biased. The source region 143a and base 141 are held at the same electrical potential and the drain is biased positive 149a with respect to the base. When the gate (reference) electrode is biased positive 149b with respect to the base, base electrons are attracted to the reference (gate) electrode 148. When this occurs, a thin conducting channel rich in electrons forms between the source and drain regions 143a and 143b. Current increases as the reference (gate) electrode 148 is made more positive. Thus, the gate potential regulates current flow between the source and the drain regions.

The essential feature of the ISFET sensor 140 is the chemically sensitive layer 146, which is typically 1 $mm^2$ in size. Silicon nitride is sensitive to $H^+$ ions, making the ISFET sensor able to measure the pH of solutions. A hydrolyzing enzyme, such as polyacrylamide containing penicillinase, placed atop the silicon nitride layer makes the ISFET sensor able to sense the presence of penicillin in solution. Thus, appropriate chemicals allow an ISFET sensor to be used to measure the concentration of particular antibodies in a solution and, thus, allows a substance concentration sensor formed in accordance with this invention to determine drug effectiveness. An ISFET sensor is capable of measuring the concentration of a particular substance in a volume of fluid as small as 5 microliters. Obviously, a response delay, which will depend on the drug being administered, must be taken into consideration.

Figure 24:
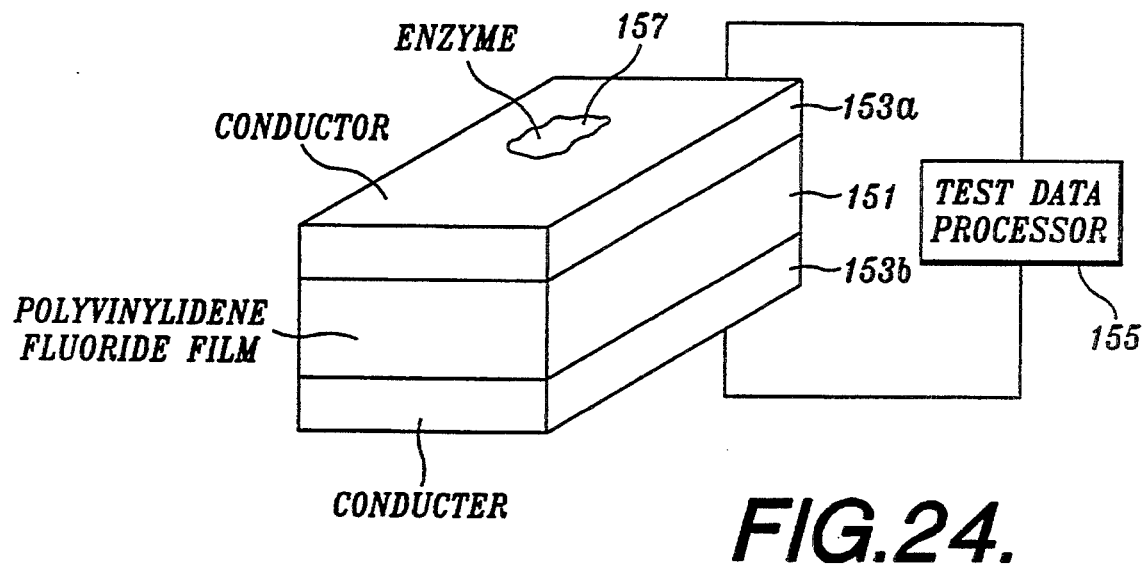
FIG. 24 is a pictorial diagram of an alternative substance sensing transducer suitable for use in the substance concentration sensor illustrated in FIG. 22.

FIG. 24 illustrates an alternate substance sensing transducer. More specifically, FIG. 24 illustrates a substance sensing transducer comprising a thin film of polyvinylidene fluoride (PVDF) 151 having a conductive layer 153a, 153b on either side. The conductive layers are connected to a data processor 155. Thin films of PVDF can be made piezoelectric or pyroelectric. A pyroelectric result occurs when a thin film of PVDF laminated on both sides with a suitable conductor is heated while a strong electric field is applied across the conductors and the film is stress oriented by stretching. The field is kept in place as the film is cooled. Coating one side of the sandwich with a suitable enzyme 157 and placing the sandwich in a solution containing the substance being tested for causes a voltage to be generated by the heat of the reaction between the enzyme and substance. The magnitude of the voltage is related to the concentration of the substance. For example, peroxide concentration can be tested for using the organic catalyst catalase as the enzyme.

Figure 25:
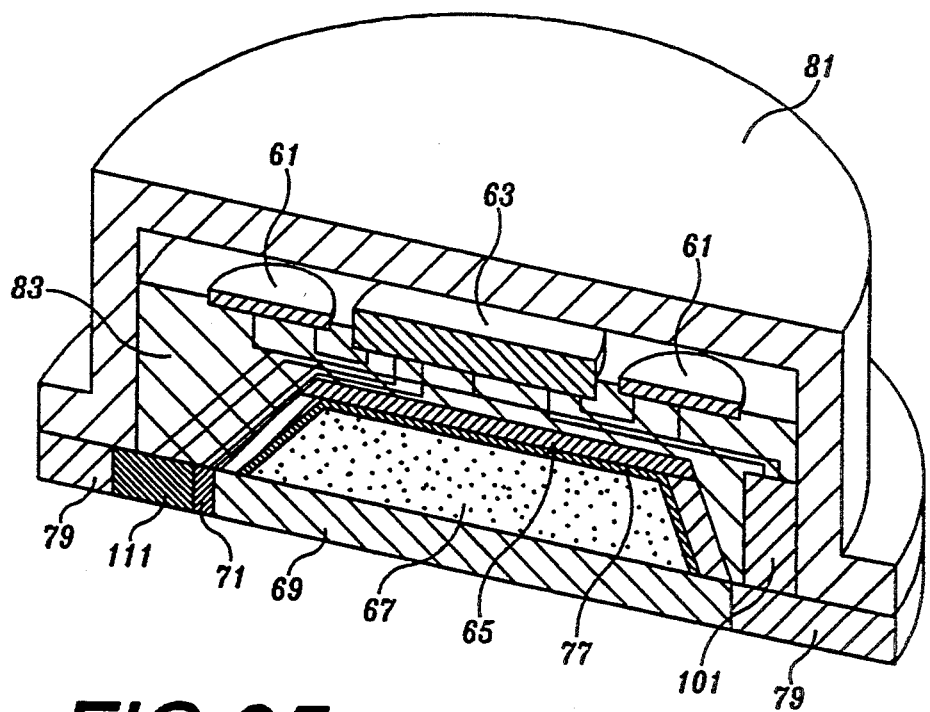
FIG. 25 is a cross-sectional, pictorial view of the structural arrangement of a further alternative embodiment of an ultrasonic transducer drug delivery system formed in accordance with the invention.

FIGS. 25 and 26 illustrate a further alternative embodiment of the invention that is similar to the embodiment of the invention illustrated in FIGS. 18–20. Since the embodiment of the invention illustrated in FIGS. 25 and 26 is generally similar to the embodiments of the invention illustrated in FIGS. 18–20, the same reference numerals are utilized to identify similar elements. The main difference between the embodiment of the invention illustrated in FIGS. 25 and 26 and the embodiment of the invention illustrated in FIGS. 18–20 is the inclusion of an IR (infrared) or laser emitter 101 similar to the IR or laser emitter included in the embodiment of the invention illustrated in FIGS. 15 and 16. Rather than being connected to the pulse sensor 102 that applies pulses to the IR or laser emitter 101 via the multiplexer 104 as in the embodiment of the invention illustrated in FIGS. 18–20, the temperature sensor 71 in the embodiment of the invention illustrated in FIG. 26 is connected to the microprocessor 116.

As shown in FIG. 27 and more fully described below with respect to FIGS. 29–32, as in the FIGS. 15 and 16 embodiment of the invention, the IR or laser emitters are controlled to produce IR or laser pulses during the period of time the variable frequency, ultrasonic pumping pulses are applied to the transducer segments 87a, 87b, 87c . . .

Figure 28:
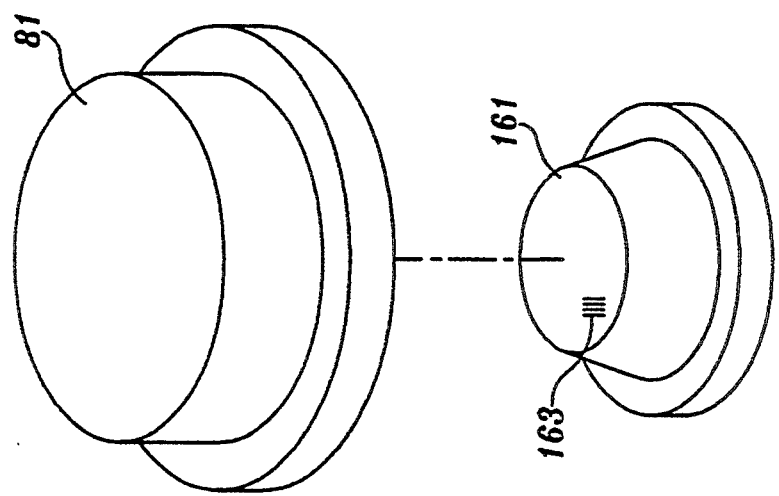
FIG. 28 is a pictorial, exploded view illustrating a replaceable drug canister portion of the embodiments of the invention shown separated from the housing.

FIG. 28 illustrates a detachable canister assembly. While suitable for use in any of the embodiments of the invention, the canister assembly is more usable in more expensive embodiments of the invention, such as those shown in FIGS. 18–20 and 25 and 26. The canister assembly includes the hat-shaped housing 81 included in all of the illustrated embodiments of the invention. Permanently housed in the housing are the ultrasonic transducer assembly 65, and the various electronic subsystems heretofore described. In addition to the housing, the canister assembly includes a canister 161. The canister is formed by the elements that surround the reservoir 67 in which the drug to be delivered is located. Specifically, the canister is formed by the drug-impermeable laminate 77 that also functions as a focusing lens and the polymeric membrane 69. Suitably located on the exterior of the canister is a machine (optically, magnetically, electrically or chemically) readable code 163, such as a bar code 163. The machine readable code is read by a code reader (not shown) embedded in the housing 81. The machine readable code identifies the drug housed in the canister 161 and may include instructions regarding the dosage to be administered, acceptable skin temperature, etc.

FIG. 29 is a master flow diagram illustrating the operation of the microprocessor of the embodiment of the invention. That is, FIG. 29 is a master flow diagram illustrating how the control program controls the operation of the microprocessor of the embodiment of the invention illustrated in FIG. 26. As will be better understood from the following description, the program can be readily modified to control the microprocessor of the embodiment of the invention illustrated in FIG. 20 by eliminating unnecessary steps, namely, the steps related to the control of the IR or laser emitters 101.

Figure 30:
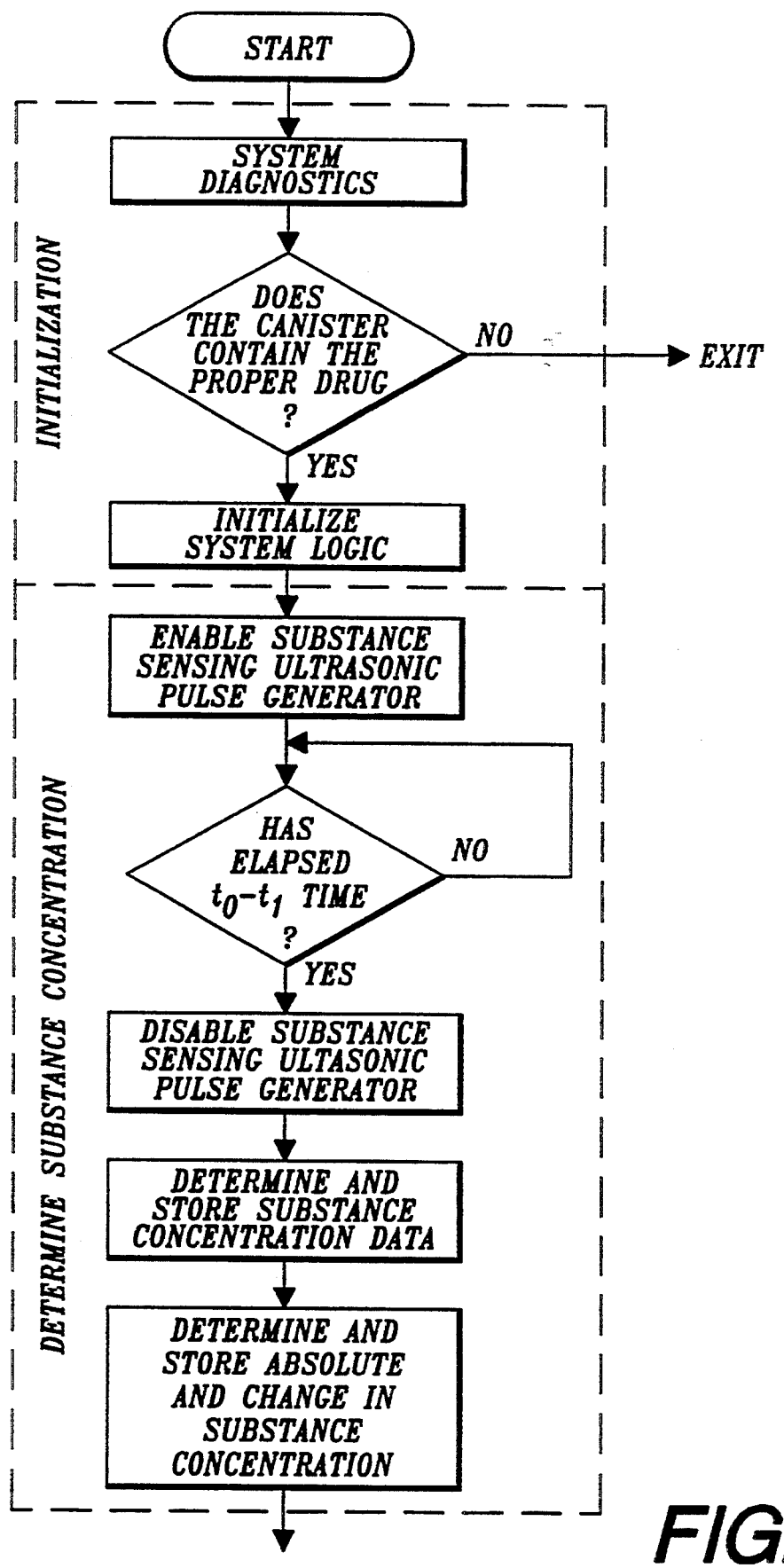
FIG. 30 is a flow diagram of the initialization and determine drug concentration portions of the master flow diagram illustrated in FIG. 29.

First, the microprocessor is initialized. As will be better understood from the following description of the initialization subroutine illustrated in FIG. 30, during initialization, a test is made to determine if the proper drug canister is present. If the proper drug canister is not present, the program ends. After the initialization subroutine, the substance concentration sensor is enabled and the substance to be tested for is detected and analyzed. After the determined drug concentration subroutine, which is also illustrated in FIG. 30 and described below, is completed, the initial skin temperature of the organism is determined. After the initial skin temperature has been determined, or this subroutine is by-passed if the initial skin temperature was previously determined, a stimuli pulse is applied to the skin. After the time period $t_1-t_2$ has elapsed, the drug is delivered. After the drug delivery cycle is ended, i.e., at $t_9$, the sequence of operation is repeated.

As illustrated in FIG. 30, the first step of the initialization subroutine is to do a conventional system diagnostic check of the microprocessor. Assuming the check is satisfactorily passed, a test is made to determine if a canister containing the proper drug is present. As noted above, if the proper drug canister is not present, the control program ends. If the proper drug canister is present, the system logic is initialized. Initialization may be based on the code contained on the drug canister. Thereafter, the program cycles to the determine substance concentration subroutine.

The first step in the determine substance concentration subroutine is to enable the substance sensing ultrasonic pulse generator 112. As previously discussed, during the period of time the substance sensing pulse generator 112 is enabled, fluids are withdrawn from the human body into the cavity 135 of the extraction transducer 126. After the substance sensing ultrasonic pulse generator has been enabled, a test is made to determine if the $t_0-t_1$ time has elapsed. If the time has not elapsed, the test is repeated. After the $t_0-t_1$ time has elapsed, the substance sensing ultrasonic pulse generator 112 is disabled. Thereafter, the drug analysis program is enabled and the substance concentration data generated by the substance sensing transducer 133 is analyzed. The results of the analysis are stored. Next, the absolute value and the change in substance concentration are determined and the results of the determination stored. Thereafter, the program cycles to the determine initial skin temperature subroutine illustrated in FIG. 31 and described next.

Figure 31:
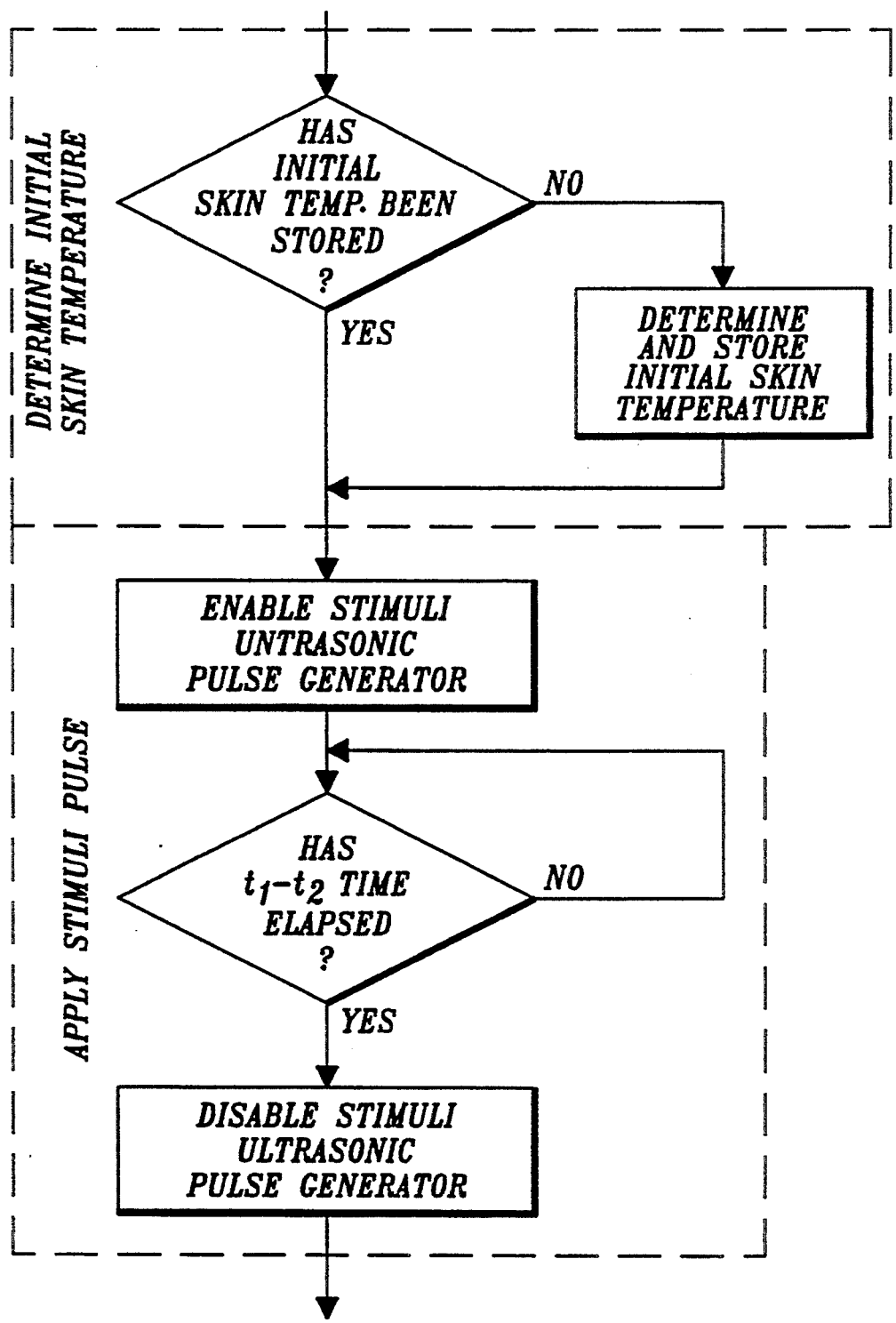
FIG. 31 is a flow diagram of the determine initial skin temperature and apply stimuli pulse portions of the master flow diagram illustrated in FIG. 30.
Figure 32:
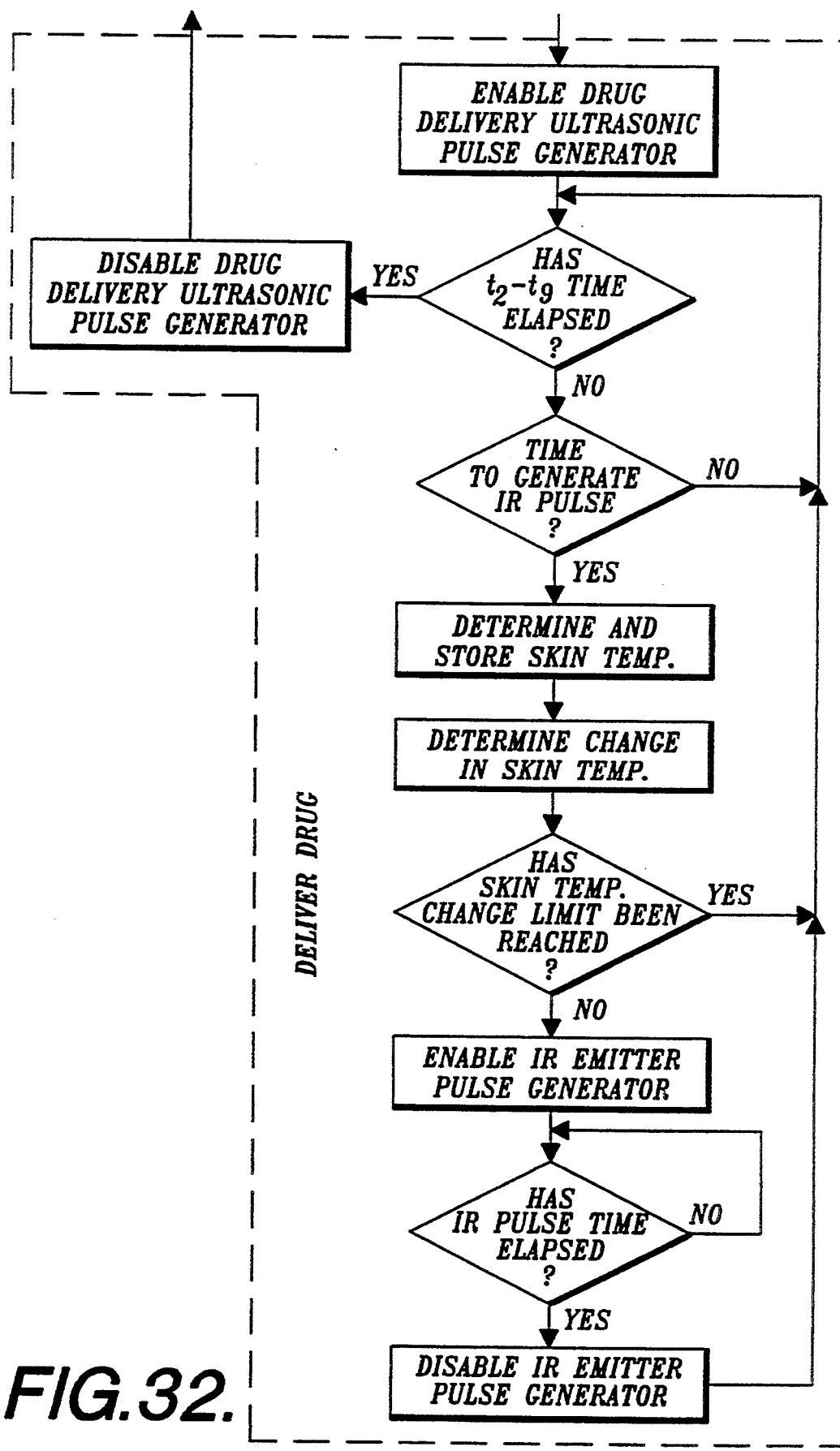
FIG. 32 is a flow diagram of the delivery drug portion of the master flow diagram illustrated in FIG. 29.

The first step in the determine initial skin temperature subroutine is a test to determine if the initial skin temperature has been stored. If the initial skin temperature has not been stored, the initial skin temperature is determined and stored. Thereafter, or if the initial skin temperature was previously stored, the program cycles to the apply stimuli pulse subroutine, which is also illustrated in FIG. 31.

The first step in the apply stimuli pulse subroutine is to enable the stimuli ultrasonic pulse generator 66 (via the pulse modulator 62) to cause stimuli pulses to be generated for application to the flat, circular (stimuli) transducer 85 by the multiplexer 68. Thereafter, a test is made to determine if the $t_1-t_2$ time period has elapsed. If the $t_1-t_2$ time period has not elapsed, the test is repeated. After the $t_1-t_2$ time period has elapsed, the stimuli ultrasonic pulse generator 66 is disabled. That is, the pulse modulator stops the pulse generator 66 from generating stimuli pulses. Thereafter, the program cycles to the deliver drug subroutine illustrated in FIG. 32 and described next.

The first step in the deliver drug subroutine is to enable the drug delivery ultrasonic pulse generator 66 via the pulse modulator 62. More specifically, the pulse modulator controls the pulse generator 66 so that variable frequency drug delivery pumping pulses are applied to the transducer segments 87a, 87b, 87c, 87d . . . in the manner heretofore described. Next a test is made to determine if the $t_2-t_9$ time period has elapsed. If the $t_2-t_9$ time period has elapsed, the drug delivery ultrasonic pulse generator 66 is again disabled and the program cycles to the initialized subroutine illustrated in FIG. 30 and described above. If the $t_2-t_9$ time period has not elapsed, a test is made to determine if it is time to generate another IR pulse. If it is not time to generate another IR pulse, the program cycles to the $t_2-t_9$ time period elapsed test.

If it is time to generate another IR pulse, the skin temperature is determined and stored. Next, the change in skin temperature from the previously recorded value is determined. Then a test is made to determine if the skin temperature change has reached a predetermined limit. If the limit has been reached, the program cycles to the $t_2-t_9$ time period elapse test. As a result, no IR pulse is generated. No IR pulse is generated because the skin temperature has reached a predetermined change limit. Rather than a change limit, an absolute temperature test can be performed or both tests can be performed.

If the skin temperature has not reached a predetermined limit, the IR emitter pulse generator 102 is enabled. Next a test is made to determine if the IR pulse time has elapsed. If the IR pulse time has not elapsed, this test is repeated. After the IR pulse time has elapsed, the IR emitter pulse generator 102 is disabled and the program cycles to the $t_2-t_9$ time period elapsed test.

As will be readily appreciated from the foregoing description, the invention provides an ultrasonic transdermal drug delivery system. The system is noninvasive since it does not require that a needle or other mechanical device invade the skin in order to deliver drugs. Rather, transdermal drug delivery systems formed in accordance with this invention use ultrasonic energy to release a stored pharmaceutical agent (e.g., a drug) and forcibly move the agent through the skin of an organism, such as the human body, into the blood vessels underlying the ultrasonic transducers that produce the ultrasonic energy. The invention can be embodied in a variety of forms. In one form, drugs are delivered in accordance with a predetermined setting. Alternative embodiments of the invention include a mechanism for determining the concentration of a particular substance in fluid withdrawn from the body, in the same or a different region of the organism from where the pharmaceutical agent is being delivered. The withdrawn fluid is analyzed and the results used to control the delivery of the pharmaceutical agent. The substance concentration sensor that removes fluid from the body and analyzes the fluid can also be provided as a stand-alone unit, i.e., a test unit independent of a drug delivery system. As with the drug delivery system, the substance concentration sensor is noninvasive, i.e., it does not use a needle or other mechanical device to withdraw fluid from the organism for analysis. Rather, the substance concentration sensor uses ultrasonic energy to forcibly remove fluid from the organism for analysis.

While preferred embodiments of the invention have been illustrated and described, it will be appreciated that various changes can be made therein without departing from the spirit of the invention. Hence, within the scope of the appended claims it is to be understood that the invention can be practiced otherwise than as expressly described herein.

The embodiments of the invention in which an exclusive property or privilege is claimed are defined as follows:

1. An ultrasonic transdermal drug delivery system comprising:
   (a) a housing;
   (b) an ultrasonic transducer assembly mounted in said housing, said ultrasonic transducer assembly including a stimuli transducer and at least one drug delivery transducer, said stimuli and said at least one drug delivery transducer oriented so as to at least partially define a reservoir having an open side for storing a pharmaceutical to be delivered;
   (c) a membrane whose porosity is controllable by ultrasonic waves positioned to close the open side of said reservoir;
   (d) attachment means for attaching said transdermal drug delivery system to an organism having a skin such that said membrane faces said skin and separates said reservoir from said skin; and
   (e) electronic control means coupled to said stimuli transducer and said at least one drug delivery transducer for causing said stimuli transducer to emit ultrasonic stimuli pulses having a frequency for a predetermined period of time and, subsequent to said predetermined period of time, causing said at least one drug delivery transducer to emit variable frequency ultrasonic pumping pulses that cause the pharmaceutical stored in said reservoir to be forcibly moved through said membrane to said skin and into said skin.

2. The ultrasonic transdermal drug delivery system claimed in claim 1, wherein said at least one drug delivery transducer is oriented such that said variable frequency ultrasonic pumping pulses intersect said skin at an oblique angle.

3. The ultrasonic transdermal drug delivery system claimed in claim 2 wherein the frequency of said ultrasonic stimuli pulses lie in a range of 5 KHz–1 MHz.

4. The ultrasonic transdermal drug delivery system claimed in claim 3 wherein the frequency of said variable frequency ultrasonic pumping pulses lie in a range of 50 MHz–300 MHz.

5. The ultrasonic transdermal drug delivery system claimed in claim 4 wherein said variable frequency ultrasonic pumping pulses are harmonics of one another.

6. The ultrasonic transdermal drug delivery system claimed in claim 5 wherein said variable frequency ultrasonic pumping pulses have a fundamental frequency that lies at the lower end of said 50 MHz–300 MHz range.

7. The ultrasonic transdermal drug delivery system claimed in claim 2 wherein the frequency of said variable frequency ultrasonic pumping pulses lie in a range of 50 MHz–300 MHz.

8. The ultrasonic transdermal drug delivery system claimed in claim 7 wherein said variable frequency ultrasonic pumping pulses are harmonics of one another.

9. The ultrasonic transdermal drug delivery system claimed in claim 8 wherein said variable frequency ultrasonic pumping pulses have a fundamental frequency that lies at the lower end of said 50 MHz–300 MHz range.

10. The ultrasonic transdermal drug delivery system claimed in claim 2, wherein said reservoir includes walls that define a truncated geometric shape and said ultrasonic drug delivery system includes a plurality of drug delivery transducer segments, said plurality of drug delivery transducer segments forming at least a part of the walls of said reservoir.

11. The ultrasonic transdermal drug delivery system claimed in claim 10, wherein said truncated geometric shape is a truncated cone, and wherein said stimuli transducer defines the small end of said truncated cone and said membrane closes the larger end of said truncated cone.

12. The ultrasonic transdermal drug delivery system claimed in claim 11 wherein the frequency of said ultrasonic stimuli pulses lie in a range of 5 KHz–1 MHz.

13. The ultrasonic transdermal drug delivery system claimed in claim 12 wherein the frequency of said variable frequency ultrasonic pumping pulses lie in a range of 50 MHz–300 MHz.

14. The ultrasonic transdermal drug delivery system claimed in claim 13 wherein said variable frequency ultrasonic pumping pulses are harmonics of one another.

15. The ultrasonic transdermal drug delivery system claimed in claim 14 wherein variable frequency ultrasonic pumping pulses have a fundamental frequency that lies at the lower end of said 50 MHz–300 MHz range.

16. The ultrasonic transdermal drug delivery system claimed in claim 11 wherein the frequency of said variable frequency ultrasonic pumping pulses lie in a range of 50 MHz–300 MHz.

17. The ultrasonic transdermal drug delivery system claimed in claim 16 wherein said variable frequency ultrasonic pumping pulses are harmonics of one another.

18. The ultrasonic transdermal drug delivery system claimed in claim 17 wherein said variable frequency ultrasonic pumping pulses have a fundamental frequency that lies at the lower end of said 50 MHz–300 MHz range.

19. The ultrasonic transdermal drug delivery system claimed in claim 11 including a drug-impermeable laminate located between said reservoir and said stimuli transducer and said plurality of drug delivery transducer segments.

20. The transdermal drug delivery system claimed in claim 19, wherein said drug-impermeable laminate also functions as a focusing lens for said stimuli transducer and said plurality of drug delivery transducer segments.

21. The ultrasonic transdermal drug delivery system claimed in claim 20 wherein the frequency of said ultrasonic stimuli pulses lie in a range of 5 KHz–1 MHz.

22. The ultrasonic transdermal drug delivery system claimed in claim 21 wherein the frequency of said variable frequency ultrasonic pumping pulses lie in a range of 50 MHz–300 MHz.

23. The ultrasonic transdermal drug delivery system claimed in claim 22 wherein said variable frequency ultrasonic pumping pulses are harmonics of one another.

24. The ultrasonic transdermal drug delivery system claimed in claim 23 wherein said variable frequency ultrasonic pumping pulses have a fundamental frequency that lies at the lower end of said 50 MHz–300 MHz range.

25. The ultrasonic transdermal drug delivery system claimed in claim 20 wherein the frequency of said variable frequency ultrasonic pumping pulses lie in a range of 50 MHz–300 MHz.

26. The ultrasonic transdermal drug delivery system claimed in claim 25 wherein said variable frequency ultrasonic pumping pulses are harmonics of one another.

27. The ultrasonic transdermal drug delivery system claimed in claim 26 wherein said variable frequency ultrasonic pumping pulses have a fundamental frequency that lies at the lower end of said 50 MHz–300 MHz range.

28. The ultrasonic transdermal drug delivery system claimed in claim 20, wherein said plurality of drug delivery transducer segments total an even number, and wherein pairs of drug delivery transducer segments are positioned on opposite sides of said truncated cone.

29. The ultrasonic transdermal drug delivery system claimed in claim 28 wherein said pairs of drug delivery transducer segments positioned on opposite sides of said truncated cone are simultaneously energized to emit variable frequency ultrasonic pumping pulses.

30. The ultrasonic transdermal drug delivery system claimed in claim 29 wherein the frequency of said ultrasonic stimuli pulses lie in a range of 5 KHz–1 MHz.

31. The ultrasonic transdermal drug delivery system claimed in claim 30 wherein the frequency of said variable frequency ultrasonic pumping pulses lie in a range of 50 MHz–300 MHz.

32. The ultrasonic transdermal drug delivery system claimed in claim 31 wherein said variable frequency ultrasonic pumping pulses are harmonics of one another.

33. The ultrasonic transdermal drug delivery system claimed in claim 32 wherein said variable frequency ultrasonic pumping pulses have a fundamental frequency that lies at the lower end of said 50 MHz–300 MHz range.

34. The ultrasonic transdermal drug delivery system claimed in claim 29 wherein the frequency of said variable frequency ultrasonic pumping pulses lie in a range of 50 MHz–300 MHz.

35. The ultrasonic transdermal drug delivery system claimed in claim 34 wherein said variable frequency ultrasonic pumping pulses are harmonics of one another.

36. The ultrasonic transdermal drug delivery system claimed in claim 35 wherein said variable frequency ultrasonic pumping pulses have a fundamental frequency that lies at the lower end of said 50 MHz–300 MHz range.

37. The ultrasonic transdermal drug delivery system claimed in claim 29 wherein sequential pairs of opposed drug delivery transducer segments are simultaneously energized to emit variable frequency ultrasonic pumping pulses rotating about the central axis of said truncated cone.

38. The ultrasonic transdermal drug delivery system claimed in claim 37 wherein the frequency of said ultrasonic stimuli pulses lie in a range of 5 KHz–1 MHz.

39. The ultrasonic transdermal drug delivery system claimed in claim 38 wherein the frequency of said variable frequency ultrasonic pumping pulses lie in a range of 50 MHz–300 MHz.

40. The ultrasonic transdermal drug delivery system claimed in claim 39 wherein said variable frequency ultrasonic pumping pulses are harmonics of one another.

41. The ultrasonic transdermal drug delivery system claimed in claim 40 wherein said variable frequency ultrasonic pumping pulses have a fundamental frequency that lies at the lower end of said 50 MHz–300 MHz range.

42. The ultrasonic transdermal drug delivery system claimed in claim 37 wherein the frequency of said variable frequency ultrasonic pumping pulses lie in a range of 50 MHz–300 MHz.

43. The ultrasonic transdermal drug delivery system claimed in claim 42 wherein said variable frequency ultrasonic pumping pulses are harmonics of one another.

44. The ultrasonic transdermal drug delivery system claimed in claim 43 wherein said variable frequency ultrasonic pumping pulses have a fundamental frequency that lies at the lower end of said 50 MHz–300 MHz range.

45. The ultrasonic transdermal drug delivery system claimed in claim 2, 11, 20, 29 or 37 including an energy emitter mounted in said housing adjacent said transducer assembly, said energy emitter connected to said electronic control means, said electronic control means also controlling said energy emitter such that said energy emitter produces further stimuli pulses at predetermined intervals during the period of time said variable frequency ultrasonic pumping pulses are being produced by said drug delivery transducer segments.

46. The ultrasonic transdermal drug delivery system claimed in claim 45, wherein said energy emitter is an infrared (IR) emitter.

47. An ultrasonic transdermal drug delivery system as claimed in claim 45, wherein said energy emitter is a laser emitter.

48. The ultrasonic transdermal drug delivery system claimed in claim 45, including temperature sensing means, said temperature sensing means including a temperature sensing device positioned in said housing for sensing the temperature of the skin of said organism when said transdermal drug delivery system is attached by said attachment means to an organism having a skin, said temperature sensing device connected to said electronic control means for preventing said electronic control means from causing said stimuli transducer to emit ultrasonic stimuli pulses if the temperature sensed by said temperature sensing means exceeds a predetermined parameter.

49. The ultrasonic transdermal drug delivery system as claimed in claim 48, wherein said electronic control means is inhibited from energizing said energy emitter if the temperature sensed by said temperature sensing means exceeds predetermined parameter.

50. The ultrasonic transdermal drug delivery system claimed in claim 20, 29 or 37, wherein said drug delivery reservoir is part of a canister that also includes said membrane and said drug-impermeable laminate.

51. The ultrasonic transdermal drug delivery system as claimed in claims 2, 11, 20, 29 or 37, including a substance concentration sensor for withdrawing fluid from said organism and analyzing said fluid to determine the concentration of a particular component of said fluid, and wherein said electronic means controls the delivery of drugs based on said concentration determination.

52. The ultrasonic transdermal drug delivery system claimed in claim 51, wherein said substance concentration sensor includes:
(a) an ultrasonic sensor transducer for generating ultrasonic sensing pulses when energized;
(b) energizing means for energizing said ultrasonic sensor transducer;
(c) focusing means, including a cavity adjacent the skin of said organism when said transdermal drug delivery system is attached by said attachment means to an organism having skin, for focusing the ultrasonic sensing pulse is generated by said ultrasonic sensor transducer into said organism, said ultrasonic sensing pulses focused by said focusing means causing fluid to be withdrawn from said organism through said skin into said cavity;
(d) a substance sensing transducer mounted in said cavity for sensing a substance in said fluid; and
(e) analysis means coupled to said substance sensing transducer for determining the concentration of said substance sensed by said substance sensing transducer.

53. The ultrasonic transdermal drug delivery system claimed in claim 52, wherein said ultrasonic sensor transducer is planar and lies in a plane parallel to a surface of the skin of said organism.

54. The ultrasonic transdermal drug delivery system claimed in claim 53, wherein said focusing means is a plano-concave lens positioned such that the concave side of said lens faces the skin of said organism and said ultrasonic sensor transducer is located on the plano side of said plano-concave lens.

55. The ultrasonic transdermal drug delivery system claimed in claim 54, wherein said substance sensing transducer is an ISFET.

56. The ultrasonic transdermal drug delivery system claimed in claim 54, wherein said substance sensing transducer is a sandwich formed of a polyvinylidene fluoride film located between two layers of conductive material.

57. The ultrasonic transdermal drug delivery system claimed in claim 52, wherein said focusing lens is a plano-concave means positioned such that the concave side of said lens faces the skin of said organism and said transducer is located on the plano side of said plano-concave lens.

58. The ultrasonic transdermal drug delivery system claimed in claim 57 wherein the frequency of said ultrasonic stimuli pulses lie in a range of 5 KHz–1 MHz.

59. The ultrasonic transdermal drug delivery system claimed in claim 58 wherein the frequency of said variable frequency ultrasonic pumping pulses lie in a range of 50 MHz–300 MHz.

60. The ultrasonic transdermal drug delivery system claimed in claim 59 wherein said variable frequency ultrasonic pumping pulses are harmonics of one another.

61. The ultrasonic transdermal drug delivery system claimed in claim 60 wherein said variable frequency ultrasonic pumping pulses have a fundamental frequency that lies at the lower end of said 50 MHz–360 MHz range.

62. The ultrasonic transdermal drug delivery system claimed in claim 61 wherein the frequency of said ultrasonic sensing pulses lie in a range of 3 MHz–50 MHz.

63. The ultrasonic transdermal drug delivery system claimed in claim 57 wherein the frequency of said variable frequency ultrasonic pumping pulses lie in a range of 50 MHz–300 MHz.

64. The ultrasonic transdermal drug delivery system claimed in claim 63 wherein said variable frequency ultrasonic pumping pulses are harmonics of one another.

65. The ultrasonic transdermal drug delivery system claimed in claim 64 wherein said variable frequency ultrasonic pumping pulses have a fundamental frequency that lies at the lower end of said 50 MHz–300 MHz range.

66. The ultrasonic transdermal drug delivery system claimed in claim 65 wherein the frequency of said ultrasonic sensing pulses lie in a range of 3 MHz–50 MHz.

67. A transdermal drug delivery method comprising the steps of:
(a) placing a reservoir containing a pharmaceutical on a region of the skin of an organism having a skin;
(b) applying ultrasonic stimuli pulses to said skin in the region where said reservoir is placed for a first predetermined period of time;
(c) applying variable frequency ultrasonic drug delivery pulses to said skin in said region where said reservoir is placed for a second predetermined period of time subsequent to said first predetermined period of time; and
(d) sequentially repeating the steps of applying ultrasonic stimuli pulses followed by the step of applying variable frequency ultrasonic drug delivery pulses to the skin of said organism.

68. The method claimed in claim 67, wherein said ultrasonic stimuli pulses are applied perpendicular to said skin.

69. The method claimed in claim 68, wherein said variable frequency ultrasonic drug delivery pulses are applied to said skin at an oblique angle.

70. The method claimed in claim 69, wherein a pair of variable frequency ultrasonic drug delivery pulses are simultaneously applied to said skin at oblique angles from opposed directions.

71. The method claimed in claim 70, wherein said pair of obliquely applied variable frequency ultrasonic drug delivery pulses are applied in a rotating manner about a common center.

72. The method claimed in claim 67, 68, 69, 70 or 71, wherein said ultrasonic stimuli pulses have a frequency in a range of 5 KHz–1 MHz.

73. The method claimed in Claim 72, wherein said variable frequency ultrasonic drug delivery pulses have a frequency in a range of 50 MHz–300 MHz.

74. The method claimed in claim 73 wherein said variable frequency ultrasonic drug delivery pulses are harmonics.

75. The method claimed in claim 74 wherein said variable frequency ultrasonic drug delivery pulses have a fundamental frequency that lies at the lower end of said 50 MHz–300 MHz range.

76. The method claimed in claim 67, 68, 69, 70 or 71, wherein said variable frequency ultrasonic drug delivery pulses have a frequency in a range of 50 MHz–300 MHz.

77. The method claimed in claim 76 wherein said variable frequency ultrasonic drug delivery pulses are harmonics.

78. The method claimed in claim 77 wherein said variable frequency ultrasonic drug delivery pulses have a fundamental frequency that lies at the lower end of said 50 MHz–300 MHz range.

79. The method claimed in claim 67, 68, 69, 70 or 71, including the additional step of applying further stimuli pulses to the skin of said organism during the period of time said variable frequency ultrasonic drug delivery pulses are applied to said organism.

80. The method claimed in claim 79, wherein said ultrasonic stimuli pulses have a frequency in a range of 5 KHz–1 MHz.

81. The method claimed in claim 80, wherein said variable frequency ultrasonic drug delivery pulses have a frequency in a range of 50 MHz–300 MHz.

82. The method claimed in claim 81 wherein said variable frequency ultrasonic drug delivery pulses are harmonics.

83. The method claimed in claim 82 wherein said variable frequency ultrasonic drug delivery pulses have a fundamental frequency that lies at the lower end of said 50 MHz–300 MHz range.

84. The method claimed in claim 83, wherein said further stimuli pulses are infrared energy pulses.

85. The method claimed in claim 83, wherein said further stimuli pulses are laser pulses.

86. The method claimed in claim 79, wherein said variable frequency ultrasonic drug delivery pulses have a frequency in a range of 50 MHz–300 MHz.

87. The method claimed in claim 86 wherein said variable frequency ultrasonic drug delivery pulses are harmonics.

88. The method claimed in claim 87 wherein said variable frequency ultrasonic drug delivery pulses have a fundamental frequency that lies at the lower end of said 50 MHz–300 MHz range.

89. The method claimed in claim 88, wherein said further stimuli pulses are infrared energy pulses.

90. The method claimed in claim 88, wherein said further stimuli pulses are laser pulses.

91. The method claimed in claim 79 including the steps of detecting the temperature of the skin of said organism and terminating the application of said further stimuli pulses when the temperature of the skin of said organism exceeds a predetermined parameter.

92. The method claimed in claim 67, 68, 69, 70 or 71, including the steps of: withdrawing fluid from said organism; and using the results of said determination to control the application of said ultrasonic stimuli pulses and said ultrasonic drug delivery pulses to said organism.

93. The method claimed in claim 92, wherein said step of withdrawing fluid from said organism is performed in a noninvasive manner.

94. The method claimed in claim 93, wherein said ultrasonic stimuli pulses have a frequency in a range of 5 KHz–1 MHz.

95. The method claimed in claim 94, wherein said variable frequency ultrasonic drug delivery pulses have a frequency in a range of 50 MHz–300 MHz.

96. The method claimed in claim 95 wherein said variable frequency ultrasonic drug delivery pulses are harmonics.

97. The method claimed in claim 96 wherein said variable frequency ultrasonic drug delivery pulses have a fundamental frequency that lies at the lower end of said 50 MHz–300 MHz range.

98. The method claimed in claim 97, including the additional step of applying further stimuli pulses to the skin of said organism during the period of time said variable frequency ultrasonic drug delivery pulses are applied to said organism.

99. The method claimed in claim 98, wherein said further stimuli pulses are infrared energy pulses.

100. The method claimed in claim 98, wherein said further stimuli pulses are laser pulses.

101. The method claimed in claim 94, wherein said variable frequency ultrasonic drug delivery pulses have a frequency in a range of 50 MHz–300 MHz.

102. The method claimed in claim 101 wherein said variable frequency ultrasonic drug delivery pulses are harmonics.

103. The method claimed in claim 102 wherein said variable frequency ultrasonic drug delivery pulses have a fundamental frequency that lies at the lower end of said 50 MHz–300 MHz range.

104. The method claimed in claim 103, including the additional step of applying further stimuli pulses to the skin of said organism during the period of time said variable frequency ultrasonic drug delivery pulses are applied to said organism.

105. The method claimed in claim 104, wherein said further stimuli pulses are infrared energy pulses.

106. The method claimed in claim 104, wherein said further stimuli pulses are laser pulses.

107. The method claimed in claim 93, wherein said substep of withdrawing fluid from said organism comprises the substeps of creating a cavity above the skin of said organism and applying ultrasonic sensing pulses to the skin of said organism beneath said cavity.

108. The method claimed in claim 107, wherein said ultrasonic stimuli pulses have a frequency in a range of 5 KHz–1 MHz.

109. The method claimed in claim 108, wherein said variable frequency ultrasonic drug delivery pulses have a frequency in a range of 50 MHz–300 MHz.

110. The method claimed in claim 109, wherein said variable frequency ultrasonic drug delivery pulses are harmonics.

111. The method claimed in claim 110, wherein said variable frequency ultrasonic drug delivery pulses have a fundamental frequency that lies at the lower end of said 50 MHz–300 MHz range.

112. The method claimed in claim 111, including the additional step of applying further stimuli pulses to the skin of said organism during the period of time said variable frequency ultrasonic drug delivery pulses are applied to said organism.

113. The method claimed in claim 112, wherein said further stimuli pulses are infrared energy pulses.

114. The method claimed in claim 112, wherein said further stimuli pulses are laser pulses.

115. The method claimed in claim 107, wherein said variable frequency ultrasonic drug delivery pulses have a frequency in a range of 50 MHz–300 MHz.

116. The method claimed in claim 115, wherein said variable frequency ultrasonic drug delivery pulses are harmonics.

117. The method claimed in claim 116, wherein said variable frequency ultrasonic drug delivery pulses have a fundamental frequency that lies at the lower end of said 50 MHz–300 MHz range.

118. The method claimed in claim 117, including the additional step of applying further stimuli pulses to the skin of said organism during the period of time said variable frequency ultrasonic drug delivery pulses are applied to said organism.

119. The method claimed in claim 118, wherein said further stimuli pulses are infrared energy pulses.

120. The method claimed in claim 118, wherein said further stimuli pulses are laser pulses.

* * * * *

UNITED STATES PATENT AND TRADEMARK OFFICE
CERTIFICATE OF CORRECTION

PATENT NO. : 5,421,816
DATED : June 6, 1995
INVENTOR(S) : L.M. Lipkovker

It is certified that error appears in the above-indentified patent and that said Letters Patent is hereby corrected as shown below:

Title page, item [57], Abstract, col. 2, line 37, "through, skin" should read -- through skin--
Column 5, line 12, "fiat" should read--flat--
Column 5, line 15, "fiat" should read --flat--
Column 11, line 15, "fiat," should read --flat--
Column 25, claim 52, line 11 , "having skin, " should read--having a skin,--
Column 25, claim 61, line 4, "360" should read --300--

Signed and Sealed this

Twenty-sixth Day of September, 1995

Attest:

BRUCE LEHMAN

Attesting Officer     Commissioner of Patents and Trademarks